Figure 1:
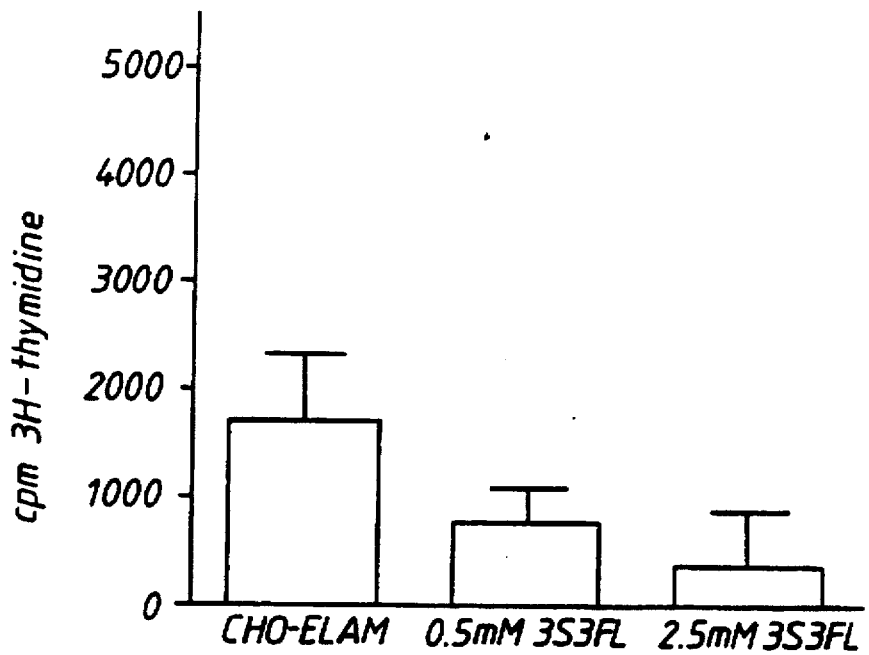

United States Patent [19]
Allanson et al.

[11] Patent Number: 5,703,059
[45] Date of Patent: Dec. 30, 1997

[54] DISACCHARIDE LIGANDS FOR SELECTINS

[75] Inventors: Nigel Mark Allanson; Alan Hornsby Davidson, both of Cowley, Great Britain

[73] Assignee: British Biotech Pharmaceuticals Ltd., Oxford, Great Britain

[21] Appl. No.: 492,002

[22] PCT Filed: Jan. 19, 1994

[86] PCT No.: PCT/GB94/00088

§ 371 Date: Apr. 12, 1996

§ 102(e) Date: Apr. 12, 1996

[87] PCT Pub. No.: WO94/17084

PCT Pub. Date: Aug. 4, 1994

[30] Foreign Application Priority Data

Jan. 19, 1993 [GB] United Kingdom ............ 9300989

[51] Int. Cl.$^6$ .................. A61K 31/715; C07H 15/00
[52] U.S. Cl. .................. 514/53; 536/123.13; 536/17.2; 514/25
[58] Field of Search .................. 536/123.13, 17.2; 514/25, 53

[56] References Cited

FOREIGN PATENT DOCUMENTS

WO9218610 10/1992 WIPO.

OTHER PUBLICATIONS

Lasky *Science* Nov. 6, 1992, 258, 964–969.
Hindsgaul, et al., Canadian Journal of Chemistry, vol. 63:2653–2658 (1985).
Allanson, et al., Tetrahedron Letters, vol. 34, No. 24:3945–3948 (1993).

*Primary Examiner*—Kathleen K. Fonda
*Attorney, Agent, or Firm*—Hale and Dorr LLP

[57] ABSTRACT

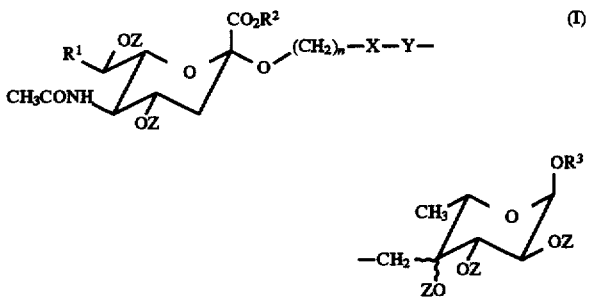

Compounds of formula (I), or a salt, solvate or hydrate thereof, wherein Z represents a divalent group selected from those of formulae I(a) to I(g) defined in the specification; Y represents a single bond or a divalent group selected from those of formulae I(h) to I(j) defined in the specification; each Z independently represents hydrogen or a hydroxyl protecting group; $R^1$ represents hydrogen or a group —CH(OZ)CH$_2$(OZ) wherein Z has the meaning defined above; $R^2$ represents hydrogen, a pharmaceutically acceptable cation, $C_{1-6}$ alkyl, $C_{2-6}$ alkenyl, or (optionally substituted)phenyl-($C_{1-4}$) alkyl; and $R^3$ represents hydrogen, $C_{1-6}$ alkyl, ($C_{1-4}$) alkyl-substituted phenyl or benzoate; and n is 1, 2 or 3. The compounds are ligands of E-, P-, and L-selectins and are useful as anti-inflammatory agents and as agents for the control of tumour metastasis.

21 Claims, 2 Drawing Sheets

DISACCHARIDE LIGANDS FOR SELECTINS

This is the U.S. national stage entry under 35 U.S.C. § 371 of PCT/GB94/00088, filed Jan. 19, 1994.

FIELD OF THE INVENTION

This invention relates to a series of carbohydrate-based compounds which are useful as anti-inflammatory agents and as agents for the control of tumour metastasis, to the use of such compounds for those purposes, to methods for their preparation, and to pharmaceutical compositions containing them.

BACKGROUND OF THE INVENTION

The compounds of the invention are ligands of E-selectin (Endothelial Leucocyte Adhesion Molecule 1), P-selectin (GMP-140) and the L-selectin, which play a crucial role in mediating the adhesion of circulating neutrophils, memory T-cells and certain tumour cell types to cytokine-stimulated endothelial cells. This adhesion is the primary event in the processes of inflammation and metastasis in which neutrophils and tumour cells leave the circulation and infiltrate the tissue. Selectin blockade may provide a therapy for inflammatory states where injury results from an excessive accumulation of neutrophils in the tissue. In this manner, the compounds of the invention may prove beneficial in the treatment of Adult Respiratory Distress Syndrome (ARDS), asthma, reperfusion injury following myocardial infarction, stroke, transplant rejection, inflammatory bowel disease, rheumatoid arthritis and endotoxic and haemmorhagic shock. They may be of therapeutic value in the treatment of chronic skin inflammations such as psoriasis, lichen planus and non-specific contact dermatitis in which high levels of skin-homing memory T cells are implicated. Blockade of E-selectin may also reduce the metastatic potential of tumour types which carry the natural ligands for E-selectin, namely the sialyl Lewis x and sialyl Lewis a antigens.

Evidence for the role of neutrophils in the development of ARDS has been reviewed (S. C. Donnely et al, Thorax, 1992, 47, 260). Neutrophil depletion in a sheep lung model has been shown to reduce microvascular damage (A. C. Heflin, J. Clin. Invest., 1981, 68, 1253). Neutrophil influx associated with late phase response in asthmatic attacks follows a similar time course to the expression of E-selectin by bronchial tissue. In monkeys, anti E-selectin antibody inhibited neutrophil influx and decreased airway obstruction (R. H. Gundel, J. Clin. Invest., 1991, 88, 1407). Neutrophil infiltration is a key factor in reperfusion injury following local ischaemia (W. J. Dreyer et al, Circulation, 1991, 84, 400), and there are many reports of the beneficial effects of blockade (see for example M. J. Horgan, Am. J. Physiol, 1990, 259, P L 315). Inadequate tissue perfusion is also found in haemorrhagic and septic shock (reviewed by N. B. Vedder et al, Prog. Clin. Biol. Res., 1989, 299, 181), where neutrophil infiltration leads to organ damage and failure. In the baboon, septic shock was associated with high expression of the E-selectin in the lung, liver and kidneys (H. Redl, Am. J. Path., 1991, 139, 461).

Inflamed colon or small intestine in Crohn's disease and ulcerative colitis are characterised by high expression of E-selectin and corresponding influx of neutrophils and lymphocytes (M. Koizumi et al, 1992, 103, 840). There is evidence for the chronic expression of E-selectin on the vessels within rheumatoid synovium (A. E. Koch, Lab. Invest., 1991, 64, 313). Lymphocytes isolated from rheumatoid synovium show an enhanced capacity to bind to the E-selectin compared with those from peripheral blood (A. A. Postigo et al, J. Clin. Invest., 1992, 89, 1445). In chronic skin inflammations such as psoriasis, lichen planus and non-specific contact dermatitis, high levels of skin-homing memory T cells are believed to be recruited by expression of E-selectin by inflamed tissue. (L. J. Picker et al, Nature, 1991, 349, 796).

The adhesion event that occurs between circulating neutrophils and endothelial cells in response to an inflammatory stimulus is mediated by binding of leucocyte integrins toextra cellular matrix and adhesion molecules of the Ig superfamily, and by carbohydrate-lectin interactions (see T. A. Springer, Nature, 1990, 346,425). IL-1β or TNFα cause endothelial cells to upregulate basal levels of ICAM-1 (which is a ligand for LFA-1 and MAC-1), and also VCAM-1 (a ligand for VLA-4). A number of lectins also become expressed on the surface of activated endothelial cells. P-selectin is released from the Weibel-Palade bodies within 30 minutes of the cytokine stimulus and E-selectin is expressed de novo after 2 hr. E-selectin reaches a maximum level of expression of about $10^6$ molecules per cell after 6–8 hr (see Bevilacqua et al, PNAS, 1987, 84, 9238). Both E-, L- and P-selectins recognise related and in some cases identical glycosylated ligands on neutrophils. Although the interactions mediated by the integrins are much stronger than those of lectins, integrins alone are unable to bring circulating neutrophils to rest under dynamic conditions. The weaker carbohydrate-lectin interactions are required to reduce the velocity of the circulating cells and cause them to roll along the surface of the endothelium before the integrin interactions can occur. Thus under physiological conditions, the rolling of neutrophils mediated by the selectins is an obligatory step in the inflammatory process. Blockade of E-selectin by anti E-selectin antibodies has been demonstrated to prevent neutrophil rolling on endothelial cells under dynamic conditions (see T. A. Springer et al, Cell 1991, 65, 859). Similarly, anti E-selectin antibodies also prevent the adhesion of a number of cell lines derived from colon carcinoma to activated endothelium (M. P. Bevilaqua et al, Science, 1989, 243, 1160), (D. Lauri et al, J. Natl. Cancer Inst, 1991, 83, 1321).

The full repertoire of endogenous ligands of the E-, L- and P-selectins has not been determined. Nevertheless, it is clear they bind to sialylated, fucosylated glycoconjugates on leukocytic cell lines. All the structures that are reported to bind to E-selectin contain one of three tetrasaccharide carbohydrate determinants; sialyl Lewis x (sLe$^x$; Neu5Acα2-3Galβ1-4[Fucα1-3]GlcNAcβR ), sialyl Lewis a (sLe$^a$; Neu5Acα2-3Galβ1-3[Fucα1-4]GlcNAcβR), and 3' sialyl-3-fucosyl lactose (3'S3FL; Neu5Acα2-3Galβ1-4[Fucα1-3]GlcβR) (see D. Tyrrel et al, P.N.A.S., 1991, 88, 10372).

WO 92/02527 discloses a series of anti-inflammatory compounds which are ligands of E-selectin and have the structure:

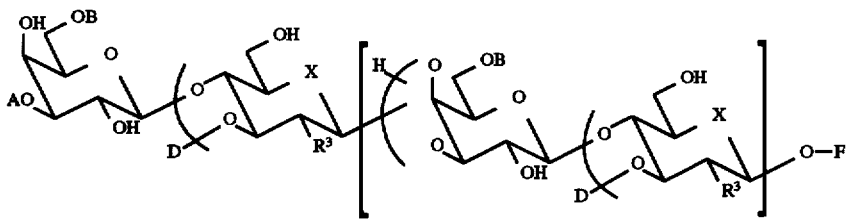

wherein each of the saccharide rings is connected by its 1 position to the 3 or 4 position of the next saccharide ring, at least one of A and B is hydrogen and the other is

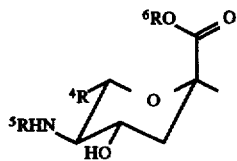

wherein: $R^4$ is —$(CHOH)_3H$, H, $C_{1-6}$ alkyl, CHO, or $C_{1-6}$ perfluoroalkyl; $R^5$ is H, $C_{1-6}$ alkyl, $COCH_3$, $COCH_2OH$, $COCF_3$; $R^6$ is H or $C_{1-6}$ alkyl; each D is independently H, a galactosyl or a fucosyl residue wherein at least one D is α-fucosyl connected to the 3 or 4 position of the sugar to which it is bound; $R^3$ is independently OH or NHAc; n is an integer from 0 to 10 with the proviso that if n is 0 and F is H then $R^3$ is OH; F is H, a ceramide residue, a linking group, a solid support, or a pharmaceutically active drug; X is oxygen, sulphur, or a group $NR^6$. At the reducing terminus of the sugar, X can also represent the dicarbinol at C-1 and C-5.

The smallest reported ligands of E-selectin are tetrasaccharides which have a molecular weight of about 1000 daltons. They contain multiple glycosidic linkages which are potentially susceptible to enzymatic degradation in vivo. Therefore, it would be desirable to design smaller synthetic ligands of E-selectin, which would not be recognised by hydrolytic enzymes for use as anti-inflammatory agents.

Although it is known that the fucose and sialic acid residues are essential for lectin-binding activity, it is not known if these residues alone are sufficient for binding, nor, if required together, in what manner they should be linked.

DESCRIPTION OF THE INVENTION

According to the present invention there is provided a compound of formula (I), or a salt, solvate or hydrate thereof:

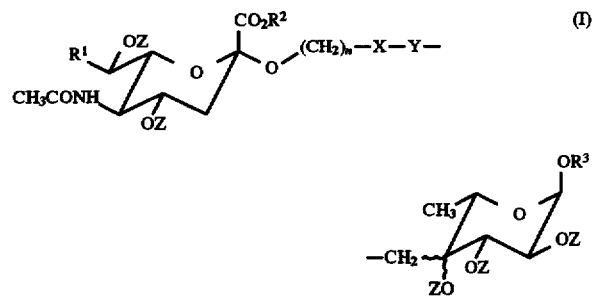

wherein:

X represents a divalent group selected from those of formulae I(a) to I(g) below —CH=CH—      I(a)

—$CH_2CH_2$—      I(b)

—CH(OH)CH(OH)—      I(c)

  I(d)

  I(e)

  I(f)

  I(g)

wherein $R_1$ and $R_2$ independently represent hydrogen, $C_{1-3}$ alkyl or —$COOR_6$ where $R_6$ is $C_{1-6}$ alkyl; $R_3$ and $R_4$ independently represent hydrogen, hydroxyl or $C_{1-3}$ alkyl; and bonds a and b may be single or double;

Y represents a single bond or a divalent group selected from those of formulae I(h) to I(j) below

  I(h)

  I(i)

  I(j)

wherein $R_5$ represents $C_{1-3}$ alkyl or a glycosyl residue;
each Z independently represents hydrogen or a hydroxyl protecting group;
$R^1$ represents hydrogen or a group —CH(OZ)$CH_2$(OZ) wherein Z has the meaning defined above;
$R^2$ represents hydrogen, a pharmaceutically acceptable cation, $C_{1-6}$ alkyl, $C_{2-6}$ alkenyl, or (optionally substituted)phenyl-($C_{1-4}$) alkyl;
$R^3$ represents hydrogen, $C_{1-6}$ alkyl, ($C_{1-4}$) alkyl-substituted phenyl or benzoate; and n is 1, 2 or 3.

In the structural formulae set out in this specification, the convention is adopted that required stereochemical orientation of any bond is as depicted except in the case of those bonds represented by a wavy line, when the bond orientation is irrelevant. Thus the methylene group attached to the Y moiety may be attached to the 4-position of the fucose ring either by an equatorial bond or an axial bond.

When any of the groupings X, Y, $R^1$, $R^2$, or $R^3$ contain asymmetric carbon atoms, the compounds of formula (I) can exist as multiple diastereoisomers, and all such diastereoisomers amd diastereomeric mixtures are incuded within the scope of this invention.

As used herein the term "$C_{1-6}$ alkyl" refers to a straight or branched chain alkyl moiety having from 1 to 6 carbon atoms, including for example, methyl, ethyl, propyl, isopropyl, butyl, isobutyl, sec-butyl, tert-butyl, pentyl, neopentyl and hexyl.

The term "$C_2-C_6$ alkenyl" refers to a straight or branched chain alkenyl moiety having from 2 to 6 carbon atoms and having in addition one or more double bond of either E or Z stereochemistry where applicable. This term would include, for example, vinyl, 1-propenyl, 1- and 2-butenyl and 2-methyl-2-propenyl.

As used herein, the term "(optionally substituted)phenyl" refers to a phenyl ring, optionally carrying one or more substituents selected from $C_{1-6}$ alkyl, hydroxyl, $C_{1-3}$ alkyl ether, acetyl, fluoro, chloro, bromo or iodo, or a group —$NX^oY^o$ where $X^o$ and $Y^o$ are independently hydrogen, oxygen, $C_{1-3}$ alkyl, or acetyl.

As used herein, the term "glycosyl residue" refers to a $C_{5-9}$ sugar attached through oxygen to its anomeric position by either an axial or an equatorial bond. In applicable glycosyl residues, both pyranosyl and furanosyl diastereoisomers are included. Illustrative of such sugar residues are the α or β forms of 1-ribosyl furanoside, 1-rhamnosyl furanoside, 1-arabinosyl furanoside, 1-glucose furanoside, 1-glucose pyranoside, 1-(2-N-acetyl)glucose pyranoside, 1-fucose pyranoside, 1-galactose pyranoside, 1-(2-N-acetyl) galactose pyranoside, 1-mannose pyranoside, 2-fructose furanoside and 2-(5-N-acetyl)neuraminic acid.

As used herein, the term "pharmaceutically acceptable cation" refers to cations which are suitable for pharmaceutical use. Examples include potasssium, sodium and lithium cations, alkali earth metal cations such as calcium and barium, and the ammonium or alkyl ammonium cations.

As used herein, the term "hydroxyl protecting group" refers to any derivative of a hydroxyl group known in the art which can be used to mask the hydroxyl group during a chemical transformation and later removed under conditions resulting in the hydroxyl group being uncovered without other undesired effects on the remainder of the molecule containing the hydroxyl group. Many esters, acetals, ketals and silyl ethers are suitable protecting groups. Representative esters include acetyl, propionyl, pivaloyl and benzoyl esters. Representative ethers include allyl, benzyl, tetrahydropyranyl, ethoxyethyl, methoxymethyl, and benzyloxymethyl ethers. Representative acetals and ketals include acetonide, ketal groups derived from cyclic ketones such as cyclohexanone, from benzaldehyde or from p-O-methoxybenzaldehyde. Representative silyl ethers include trimethylsilyl, t-butyldimethylsilyl, and t-butyldiphenylsilyl ethers.

Preferred compounds of the invention, for example for their affinity for E-selectin, are those of formula (I) in which, in any combination:

X is a group of formula I(a), I(b) or I(c);

each Z independently represents hydrogen, acetyl or benzoyl;

$R^1$ is hydrogen or —CH(OH)CH$_2$OH;

$R^2$ is methyl, hydrogen, or a sodium, lithium or potassium cation;

$R^3$ is methyl; and n is 1 or 3.

Particularly preferred compounds from the foregoing group are:

O-methyl-4R-[5'-oxy-{N-acetyl-α2"-O-neuramidinyl methyl ester}-2'-oxo-pent-1'-yl]-L-fucopyranoside;

O-methyl-4R-[{N-acetyl-α2"-O-neuramidinyl sodium carboxylate}5'oxy-2'-oxo-pent-1'-yl]-L-fucopyranoside;

O-methyl-4R-[{N-acetyl-α2"-O-neuramidinyl sodium carboxylate}5'oxy-2',3',4'-trihydroxy-pent-1'-yl]-L-fucopyranoside;

O-methyl-4R-[7'-oxy-{N-acetyl-α2"-O-neuramidinyl methyl ester}-2'-hydroxy-hept-3'-en-1'-yl]-L-fucopyranoside; and O-methyl-4R-[7'-oxy-{N-acetyl-α2"-O-neuramidinyl sodium carboxylate}-2'-hydroxy-hept-3'-en-1'-yl]-L-fucopyranoside;

The compounds of this invention may be prepared by any known method of chemical synthesis and by the methods described herein.

Preparation of Compounds of the Invention

Compounds of formula (I) wherein X is a divalent group of formula (Ia) and Y is a divalent group of formula (Ih) may be prepared by:

(a) reacting a compound of formula (II):

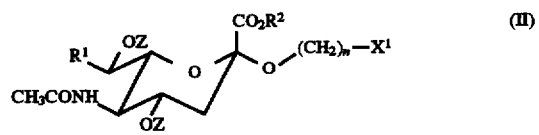

wherein n, $R^1$, $R^2$, and Z are as defined in relation to formula (I), and $X^1$ is an aldehyde group —CHO or a group —CH$_2$L wherein L is a leaving group, with a compound of formula (III):

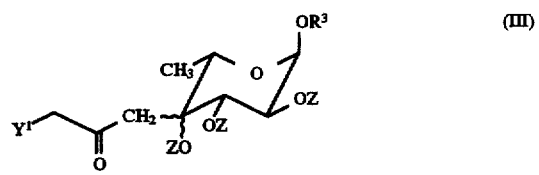

wherein $R^3$ and Z are as defined in relation to formula (I) and $Y^1$ represents an activating group for the methylene group to which it is attached, to form an intermediate of formula (IV)

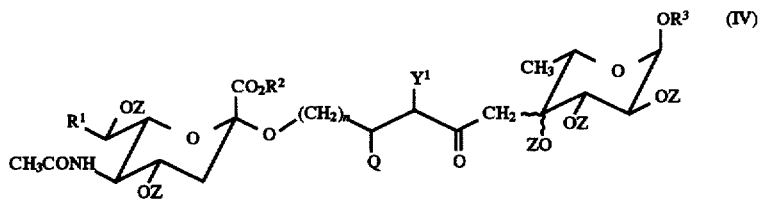

wherein n, $R^1$, $R^2$, $R^3$, Z and $Y^1$ are as defined in relation to formulae (II) and (III) and Q is OH (when $X^1$ in formula (II) is —CHO) or H (when $X^1$ in formula (II) is a group —$CH_2L$ wherein L is a leaving group);

and then (b) forming a double bond between the carbon atoms carrying the groups Q and $Y^1$ by (in cases where $X^1$ in compound (II) is an aldehyde group —CHO) allowing the said intermediate product to eliminate sponaneously the elements of Q (i.e. OH) and $Y^1$, or treating the said intermediate product to eliminate the elements of Q (i.e. OH) and $Y^1$, or (in cases where $X^1$ in compound (II) is a group —$CH_2L$ wherein L is a leaving group) treating the said intermediate product to eliminate the elements of Q (i.e. H) and $Y^1$;

and if desired (c) in the resultant compound of formula (I), removing one or more hydroxyl protecting groups Z, and/or hydrolysing any ester group —$CO_2R^2$ to a carboxylic acid or pharmaceutically acceptable cationic carboxylate group.

Activating groups $Y^1$ include alkyl and fluoroalkyl phosphonate, diphenyl phosphine oxide, triphenyl phosphine, phenyl sulphoxide, phenyl sulphonate, and alkyl carboxylate groups.

Leaving groups L in the alkylating agent (II) include iodo, bromo, and chloro, tosylate and mesylate groups.

In the above reaction, in cases where $X^1$ is an aldehyde group —CHO, loss of the elements of OH and $Y^1$ is spontaneous when $Y^1$ is a phosphonate, phosphine oxide, or triphenyl phosphine group. When $Y^1$ is a sulphonate group, the elements of OH and $Y^1$ may be eliminated by acetylation of the OH group and treatment with sodium amalgam in an alcoholic solvent. When $Y^1$ is a carboxylate group, the ester group may be hydrolysed, and the elements of OH and $Y^1$ may be eliminated by pyrolysis to give the desired compound of formula (I).

In the above reaction, in cases where $X^1$ is a group —$CH_2L$ wherein L is a leaving group, $Y^1$ may be a phenyl sulphoxide group, and the elements of H and the sulphoxide group may be eliminated from the resultant condensate by pyrolysis.

Except in cases where $Y^1$ is triphenylphosphine, the above condensation reactions involving starting materials (II) and (III), are preferably carried out in the presence of a base to form an enolate of the ketone (III). Except when $Y^1$ is a phosphonate, strong bases are preferred, e.g. t-, n-, and s-butyl lithium; potassium-, sodium- and lithium-HMDS; KOt-Bu; and lithium, sodium and potassium metals in alcohol. The solvent employed may be inert and aprotic, e.g. tetrahydrofuran, diethyl ether, dimothoxyethyl ether, toluene, benzene, hexane, or dimethyl sulphoxide, or alcoholic, e.g. methanol, ethanol, isopropanol or t-butanol. The temperature for deprotonation may be in the range +30° to 100° C. The aldehyde (II) or alkylating agent (IIa) may be added to the enolate of (III) at a temperature in the range −100° to −20° C., and quenched after 1 to 24 hours.

When $Y^1$ is triphenylphosphine, no additional base is required, and the reaction may be performed in any inert solvent, including dichloromethane and chloroform in addition to those listed above.

When $Y^1$ is a phosphonate, milder bases may be employed, e.g. potassium carbonate in an alcoholic solvent; or amine bases such as triethylamine, N-methyl morpholine, and N,N-diisopropylethylamine with metal halide additives such as lithium chloride, lithium bromide, magnesium chloride, and magnesium bromide. in acetonitrile; or alkali metal hydroxides and a crown ether in a two phase system such as water and dichloromethane.

When $Y^1$ in compound (III) is a phosphonate, a particularly preferred method of the invention is its reaction with an aldehyde of formula (II) as above, in the presence of caesium carbonate in t-butanol at a temperature in the range 25°–35° C. Under those conditions, particularly good yields of the reaction product may be obtained.

Compounds of formula (I) wherein X is a divalent group of formula (Ia) and Y is a bond may be prepared by coupling a sialic acid derivative of formula (V);

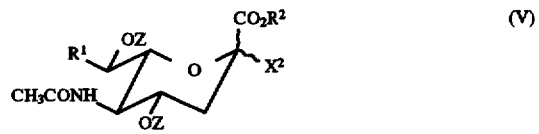

wherein $R^1$, $R^2$ and Z are as defined in formula (I) and $X^2$ is a leaving group, with an alcohol of formula (VI):

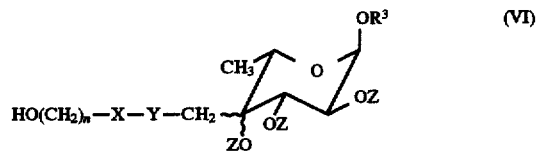

wherein n, $R^3$ and Z are as defined in formula (I), X is a divalent group of formula (Ia) above and Y is bond, and if desired removing one or more hydroxyl protecting groups Z, and/or hydrolysing any ester group —$CO_2R^2$ to a carboxylic acid or pharmaceutically acceptable cationic carboxylate group.

Suitable leaving groups $X^2$ in the sialic acid derivative of formula (V) include iodo, bromo, and chloro; sulphonyl esters such as tosylate, mesylate and triflate; sulphide groups such as methylthio and substituted phenylthio; trichloroacetimidate; and the alpha-S—(=S)—OEt and alpha-O—P (OEt)$_2$ groups.

The coupling reaction between compounds (V) and (VI) may be conducted by any of the methods known in the art for the sialylation of alcohols. A review of standard procedures for this conversion is given by M. P. DeNinno, Synthesis, 1991, 583, and additional methods are described by A. Hasegawa et al, Carb. Res., 1991,212,217, by H. Lonn et al. Tet Lett., 1992, 33, 115, and by R. R. Schmidt, et al., Tet. Lett., 1992, 33, 6123.

In the foregoing methods of preparation, removal of one or more hydroxyl protecting groups Z is an option. Any deprotection procedure may be used which known in the art as suitable for the particular hydroxyl protecting groups present in the molecule. T. W. Greene and P. G. M. Wuts "Protective groups in Organic Synthesis" 2nd Edition, J. Wiley and sons, New York, 1991 presents a general review of the methods available for the deprotection of alcohol masking groups. Thus hydrogenolysis over palladium on carbon might be employed for benzyl ethers, or tetrabutyl ammonium fluoride for silyl ethers. Particularly preferred is the removal of acyl protecting groups such as acetyl or benzoyl by a catalytic amount of $NaOR^5$ in $HOR^5$ as solvent. This allows various esters $R^5$ to be introduced into compounds of formula (I) from a common ester $R^2$ (for example methyl) in (I), at the same time as the hydroxyl groups Z in (I) are being deprotected. If more than one type of hydroxyl protecting group is present in the molecule, then using suitable deprotection procedures, partially deprotected compounds of formula (I) may be produced.

By the methods described above compounds of formula (I) wherein X is a divalent group of formula (Ia); Y is a bond or a divalent group of formula (Ih); each Z independently represents hydrogen or a hydroxyl protecting group; $R^1$ represents hydrogen or a group $—CH(OZ)CH_2(OZ)$ wherein Z has the meaning defined above; $R^2$ represents hydrogen, a pharmaceutically acceptable cation, $C_{1-6}$ alkyl, $C_{2-6}$ alkenyl, or (optionally substituted)phenyl-$(C_{1-4})$ alkyl; $R^3$ represents hydrogen, $C_{1-6}$ alkyl, $(C_{1-4})$ alkyl-substituted phenyl or benzoate; and n is 1, 2 or 3, may be prepared. Modification of those compounds, usually with all Z groups being hydroxyl protecting groups, enables the preparation of the remaining sub-classes of compounds of the invention).

Formula (I), X=(Ib), Y=(Ih)–(Ij) or a bond: prepared from corresponding compounds of formula (I), X=(Ia) by hydrogenation of the C=C double bond. This can be carried out with hydrogen or cyclohexene and a palladium on charcoal catalyst in an alcoholic solvent. Other methods known in the art may also be employed for this transformation, including other heterogenous catalysts (e.g. $PtO_2$, Pt on C, or Rh on $Al_2O_3$); or homogenous catalysts for example Wilkinson's catalyst [J. Org. Chem. 1969, 34, 3684] and hydrogen gas; dissolving metal reductions (e.g. K, Na, Li or Mg in liquid ammonia or ethanol); or metal hydride reductions (e.g. sodium hydrogen telluride [Chem. Lett. 1980, 847] or K selectride).

Formula (I), X=(Ic), Y=(Ih)–(Ij) or a bond: prepared by dihydroxylation of corresponding compounds of formula (I), X=(Ia) using $OsO_4$ according to standard methods e.g. those described in Fieser and Fieser Vol 1, pg 759–764. Alternatively they may be prepared by acidic or basic hydrolysis of corresponding compounds of formula (I), X=(Id).

Formula (I), X=(Id), Y=(Ih)–(Ij) or a bond: prepared by epoxidation of corresponding compounds of formula (I), X=(Ia), using metachloroperbenzoic acid, hydrogen peroxide or other peroxy-acids such as trifluoroperacetic acid in an inert solvent such as dichloromethane.

Formula (I), X=(Ie), Y=(Ih)–(Ij) or a bond: prepared by cyclopropanation of corresponding compounds of formula (I), X=(Ia). For X=(Ie), $R_1$ and $R_2$=H, a number of different methods may be employed: the Simmons-Smith reagent [review: Organic Reactions, 1973, 20, 1–131], the trimethylsulphoxonium ylid [Tet. Lett., 1962, 661], and the trimethylsulphonium ylid [J. Amer. Chem. Soc., 1962, 84, 3822]. For X=(Ie), $R_1$ and $R_2$=H and $—CO_2Me$, $Rh_2(OAc)_4$ (with or without other metal additives) and $N_2CHCO_2Me$ can be used [Synthesis, 1981, 787].

Formula (I), X=(If) or (Ig), Y=(Ih)–(Ij) or a bond: prepared by a Diels-Alder reaction between corresponding compounds of formula (I), X=(Ia) and suitable dienes. For example cyclopentadiene will afford adducts containing an (If) group where a is a double dond. 2,3 Disubstituted dienes will afford adducts with an (Ig) group where b is a double bond. The double bonds in these adducts can be converted to vicinal diols using $OsO_4$ or to a carbon carbon single bond by hydrogenation.

Formula (I), X=(Ia) to (Ig), Y=(Ii): prepared by reduction of the corresponding compound wherein Y=the ketone group (Ih). Any method known in the art for the reduction of a ketone to an alcohol may be used for this transformation. Examples of suitable reagents include, but are not limited to, $NaBH_4$, $NaBH_4$ and $CeCl_3$, $LiBH_4$, $LiAlH_4$, DIBAL-H, L- and K-selectrides, $Al(O-iPr)_3$, hydrogen gas and enantioselective methods such as Alpine borane, Rh-(+ or -)BINAP [Noyori et al, JCS Chem. Comm., 1988, 87] or CBS [E. J. Corey et al, J. Amer. Chem. Soc., 1987, 109, 5551]. It is preferred that compounds of formula (I) wherein X=(Ia) and Y=(Ii) or a bond are prepared from compounds of formula (I), X=(Ib), Y=(Ih) or a bond by reduction using $NaBH_4$ and $CeCl_3$ [J.-C. Luche et al., J. Amer. Chem. Soc., 1978, 100, 2226] because the carbon-carbon double bond is not reduced by this procedure.

Formula (I), X=(Ia) to (Ig), Y=(Ii): also prepared by carrying out the reduction of the ketone (Ih) to the alcohol (Ii) prior to the modification of the carbon-carbon double bond (Ia) to other derivatives (Ib)–(Ie) by the methods outlined above.

Formula (I), X=(Ia) to (Ig), Y=(Ij): prepared by reaction of known "glycosyl donors", a promoter and the corresponding compounds wherein Y=(Ii) (hydroxyl) group. The "glycosyl donor" can be, but is not limited to, 2,3,4,6 tetra-O-acetyl glucosyl bromide, 2,3,4,6 tetra-O-acetyl galactosyl bromide, 2,3,4,6 tetra-O-acetyl mannosyl bromide, 3,4,6 tri-O-acetyl-N-acetyl glucosamine chloride, 2,3,4, tri-O-benzyl fucosylbromide or methyl-4,7,8,9-tetra-O-acetyl 5-Nacetyl-neuraminidyl chloride. Representative coupling procedures are given in "Methods in Carbohydrate Chemistry", Vol II, Ed. Whistler and Wolfram, Acedemic Press Inc, New York, 1963, however, the glycosylation may be achieved by any method known in the art. These include but are not limited to, the use of silver triflate, $Ag_2CO_3$, $Ag_2O$, $HgBr_2$, $Hg(CN)_2$ in acetonitrile, toluene, benzene or dichloromethane.

Starting Materials for Compounds of the Invention

The starting materials for the reactions referred to above, i.e. compounds (II), (III), (V) and (VI) are accessible by standard synthetic methods known in the art.

Compounds of formulae (II) can be prepared in a number of simple steps from compounds of general formula (V) and commercially available (Aldrich) hydroxyalkenes; $HO(CH_2)_nCH=CH_2$, hydroxyalkylhalides (Aldrich) e.g. $HO(CH_2)_nBr$, or mono protected alkyl-diols e.g. $HO(CH_2)_{n+1}OZ$ where Z and n are as defined in formula (I). The conditions used in the reaction of compounds of formulae (V) and (VI) are also suitable for this transformation. In a preferred aspect of the invention, the reaction between a compound of formula (V):$X^2$=Cl and hydroxyalkenes is conducted in the presence of 4A sieves with the alcohol as solvent and silver salicylate as a promoter. This procedure gives mainly the desired α G glycoside. In a second step the olefinic bond is ozonolysed to yield sialyl-aldehydes of formula (II). Halides of formula (IIa) may be prepared directly by reaction of compounds of formula (V) and hydroxyalkylhalides. In this aspect $X^2$ should not also be a halide, thus suitable coupling methods include the use of protected sialyltrichloroacetimidates or -thioethers with acidic promoters.

Compounds of formula (III) above may be obtained by reaction of the dianion of compounds of general formula (VIII):

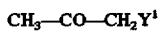    (VIII)

where Y1 is as described for compounds of formula (III), with ketones of formula (IX):

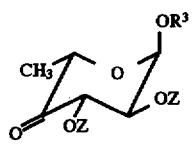    (IX)

wherein $R^3$ and Z are as defined in relation to formula (I) with the proviso that Z is not hydrogen, and subsequently optionally converting any free hydroxyl groups to protected hydroxyl groups The dianions of compounds of formula (VIII) may be obtained by reaction with two or more equivalents of a strong base in an anhydrous inert solvent in which the dianions are soluble at between –100° C. and +35° C. under an inert atmosphere. Representative procedures have been published [review: Organic Reactions, 1969, 17, 155] and J. Amer. Chem. Soc., 1973, 95, 3071]. Bases that are suitable for this reaction include tert BuLi, sec-BuLi, n-BuLi, n-BuLi and NaH, LiHMDS, NaHMDS, and KHMDS in such solvents as THF, DME, and diethyl ether. Co-mixtures with HMPA may also be used. The ketone is then added as a solution in the same solvent at between –100° C. and –20° C. and the reaction mixture is kept at this temperature for between 30 min and 5 hr. The reaction mixture is quenched at low temperature and worked up using standard procedures. Preferably, the dianion is present in a 1.5–10 fold excess, and other organometallic compounds especially $CeCl_3$ [Tet. Lett., 1984, 25, 4233] or $TiCl(Oi-Pr)_3$ [A.C.I.E.E., 1980, 19, 1011] may be added to the dianion prior to the addition of compound (IX) to improve the yield of the adduct.

Compounds of formula (III) above may also be synthesised in a variety of ways from compounds of formula (X):

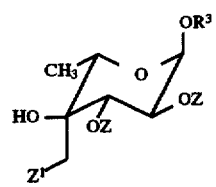    (X)

wherein $R^3$ and Z are as defined for formula 1 and $Z^1$ is a group selected from substructures Z1 to Z8:

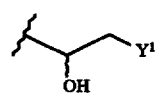    Z1

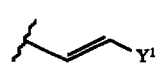    Z2

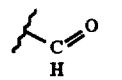    Z3

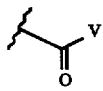    Z4

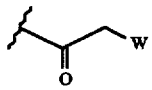    Z5

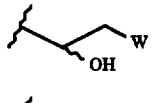    Z6

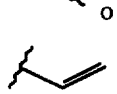    Z7

Z8 wherein W is a halogen atom, $Y^1$ is as defined in formula (III) and V represents a halogen, a methyl or ethyl ester, or a Weinreb amide —$N(OCH_3)CH_3$. [In the following section, compounds of formula (X) containing a particular $Z^1$=Z1–Z8 group are abbreviated F10(Zj) where Zj represents one of Z1–Z8].

Compounds of formula (III) as aforesaid can be prepared in one step from compounds of formula (X) where $Z^1$ is Z1–Z5, for example the reaction of:

F10(Z1) with any oxidant suitable for the oxidation of alcohols to ketones [J. March, "Advanced Organic Chemistry" 3rd edition, pg1057–1060 and references therein, J. Wiley and sons, New York 1985]. Illustrative reagents or procedures include but are not limited to the use of PCC, PDC, $Cr_2O_7$, $KMnO_4$ and the Swern and Collins oxidations;

F10(Z2) with $PdCl_2$ and $CuCl_2$ (the Wacker reaction) [review: J. Tsuji, Synthesis, 1990, 369];

F10(Z3) with $SnCl_2$ and a diazo species $N_2CHY^1$ (where $Y^1$ is —$SO_2Ph$, alkyl carboxylate, alkyl or fluoroalkyl phosphonate as defined for formula (III)) following the general procedure of E. J. Roskamp et al, Tet. Lett., 1992, 33, 1131. The syntheses of the compounds $N_2CHX$ are described in the references of this paper;

F10(Z4) with the mono or dianion of $CH_3$—$Y^1$ where $Y^1$ is as defined for formula (III). The use of strong bases and aprotic solvents as described for the conversion of compounds of general formula (VIII) to their dianions are also suitable for this transformation;

F10(Z5) heated with trialkylphosphites (Arbuzov reaction), or triphenyl phosphorane (formation of a Wittig reagent; the adduct of which can be hydrolysed with base to obtain Horner Emmons reagents). Also F10(Z5) can be reacted with $NaSO_2Ph$ or sodium dialkyl or difluoroalkyl phosphate (Michaelis-Becker reaction) to give (III);

F10(Z1) may be prepared either from F10(Z3) by reaction with the anion of $CH_3$—$Y^1$, or, where $Y^1$ is a dialkyl or difluoroalkyl phosphate group, by an Arbuzov reaction between F10(Z6) or F10(Z7) with trialkylphosphite.

F10(Z2) may be prepared by condensation reaction of F10(Z3) with $Y^1$—$CH_2$—$Y^1$ (where $Y^1$ is as previously defined)[S.-K. Chung et al., JCS Chem. Comm., 1992, 77]. Alternatively it may be prepared by reaction of compounds of general formula (IX) with compounds of general formula $R^9_3Si$—CH(X)—CH=$CH_2$ ($R^9$ is $C_{1-6}$ alkyl or phenyl) with a Lewis acid promoter such as $TiCl_4$, $SnCl_4$ or $BF_3.Et_2O$ in any inert solvent such as dichloromethane.

F10(Z3) may be prepared by ozonolysis of F10(Z8).

F10(Z4) may be prepared from F10(Z8) by a number of methods suitable for the conversion of alkenes to carboxylic acid derivatives bearing one less carbon. Illustrative procedures include ozonolysis with oxidative workup e.g. heating with $H_2O_2$ in acetic acid [Chem. Rev., 1958, 58, 925] or with triethylamine and acetic anhydride [S. L. Screiber et al., Tet. Lett., 1982, 23, 3867]. The acid so obtained can be converted to esters or acid halides by standard procedures known in the art. In a preferred aspect of the invention, F10(Z8) can be reacted with $RuCl_3$ and $NaIO_4$ following the general procedure of K. B. Sharpless et al., J. Org. Chem., 1981, 46, 3936.

In a preferred method, F10(Z5) is prepared by oxidation of F10(Z6) by any method known in the art which is suitable for the oxidation of alcohols to ketones. PCC and 4A molecular sieves in dichloromethane is illustrative of these procedures.

F10(Z6) can be prepared from F10(Z8) by standard procedures known in the art for the conversion of alkenes to halohydrins [review of methods: R. C. Larock, Comprehensive Organic Transformations, pg 325-327, VCH publishers, New York, 1989]. Alternatively F10(Z6) can be prepared by methods known in the art for the opening of epoxides F10(Z7) with halide salts [review of methods: R. C. Larock, Comprehensive Organic Transformations, pg 349, VCH publishers, New York, 1989]. In a preferred aspect of the invention, F10(Z7) is reacted with $Li_2NiBr_4$ in THF following the procedure of J. V. Turner, Tet. Lett., 1984, 25. 2061.

F10(Z7) is obtained by the reaction of F10(Z8) by epoxidation with metachloroperbenzoic acid or magnesium monoperoxyphthallate (MMPP) in an inert solvent such as dichloromethane.

In a preferred method F10(Z8) is prepared by reaction of ketones of general formula (IX) with allylsilanes $R^9{}_3Si$—$CH_2$—$CH=CH_2$ (where $R^9$ represents $C_{1-6}$ alkyl or phenyl) with a Lewis acid promoter or TBAF in an inert solvent at between $-78°$ C. and $+30°$ C. Representative procedures are reviewed in Organic Reactions, 1989, Vol 37, pg 2. These reactions give almost exclusively the axial homoallylic alcohol in high yield.

Compounds of general formula (IX) can be prepared by oxidation of compounds of general formula (XI):

(XI)

wherein $R^3$ and Z are as defined for formula (I), by any methods known in the art for the oxidation of alcohols to ketones. Representative procedures are reviewed in [J. March, "Advanced Organic Chemistry" 3rd edition, pg1057-1060 and references therein, J. Wiley and sons, New York 1985].

Some compounds of general formula (XI) are known. [J. Thiem et al., Carb. Res., 1991, 209, 119-129] describe the synthesis of α-methyl-2,3-di-O-benzoyl fucopyranoside from commercially available L-fucose (Aldrich). α-Methyl 2,3-di-O-benzyl fucose pyranoside is also known. Other compounds of this general formula with different hydroxyl protecting groups Z and different anomeric glycosides $R^3$ can be prepared by a two step process from fucose. L-fucose is first reacted with an alcohol HO—$R^3$ (where $R^3$ is as defined for formula (I)) with an acid catalyst such as Dowex $H^+$ resin to obtain a mixture of fucosyl glycosides containing a 1-O—$R^3$ group. The desired α-O $R^3$ fucopyranoside can be isolated from this mixture and then differentially protected with the desired hydroxyl protecting group Z in a one or multi-step procedure to obtain compounds of general formula (IX). Preferred aspects of this invention are the use of benzoyl chloride in pyridine following the general procedure of [J. Thiem et al., Carb. Res., 1991, 209, 119-129], or the use of 2,2'-bistetrahydropyran following the general procedure of S. Ley et al., Synthesis, 1992, 52.

Preferred examples of compounds of general formula (V) have been published [R. Roy et al, J. Carb. Chem., 1987, 6, 161]. Where $R^1$ is hydrogen, representative syntheses have been published by [Hasegawa et al, J. Carb. Chem., 1989, 8, 125] and [R. Roy et al, Can. J. Chem., 1990, 64, 2045].

Compounds of formula (VI) above may be prepared by the reaction of a compound of formula (VII):

wherein Z, n, and X are as defined in relation to formula (II), with a compound of formula (III) as defined above, with the proviso that any hydroxyl protecting group Z in compound (III) is a different protecting group from any that in compound (VII). This reaction is analagous to the above described reaction of compounds (II) and the above discussion is thus relevant in this case also.

Compounds of formula (VI) above also result from the reaction of compounds of general formula ZO—$(CH_2)_n$—$CH=CH$—$C(OSiMe_3)=CH_2$ and a Lewis acid with compounds of general formula (IX). Z and n are as defined in formula (I). A second method is by reaction of compounds of formula (IX) with compounds of general formula ZO—$(CH_2)_{n-1}$—$CH(SiMe_3)$—$CH=CH_2$ and a Lewis acid promoter. A third route is the Schlosser-Wittig reaction between compounds of general formula HO—$(CH_2)_n$—$PPh_3$ Br and compounds of general formula (X) containing a Z3 group.

Pharmaceutical Aspects of the Invention

As mentioned above, compounds of formula (I) are useful in human or veterinary medicine since they are ligands of E-, P- and L-selectins.

Accordingly in another aspect, this invention concerns:

(i) a method of management (by which is meant treatment or prophylaxis) of diseases or conditions mediated by excessive accumulation of neutrophils in the tissue in mammals, and/or metastasis in which neutrophils or tumour cells leave the circulation and infiltrate the tissue in mammals, in particular in humans, which method comprises administering to the mammal an effective amount of a compound of formula (I) above, or a pharmaceutically acceptable salt, hydrate or solvate thereof; and (ii) a compound of formula (I), or a pharmaceutically acceptable salt, hydrate or solvate thereof, for use in human or veterinary medicine, particularly in the management (by which is meant treatment or prophylaxis) of diseases or conditions mediated by excessive accumulation of neutrophils in the tissue, and/or metastasis in which neutrophils or tumour cells leave the circulation and infiltrate the tissue; and (iii) the use of a compound of formula (I) in the preparation of an agent for the management (by which is meant treatment or prophylaxis) of diseases or conditions mediated by excessive accumulation of neutrophils in the tissue in mammals and or metastasis in which neutrophils or tumour cells leave the circulation and infiltrate the tissue.

The diseases or conditions referred to above include inflammatory conditions and tumour metastases. Specific conditions included are Adult Respiratory Distress Syndrome (ARDS), asthma, reperfusion injury following myocardial infarction, stroke, transplant rejection, inflammatory bowel disease, rheumatoid arthritis and endotoxic and haemmorhagic shock, chronic skin inflammations such as psoriasis, lichen planus and non-specific contact dermatitis in which high levels of skin-homing memory T cells are implicated. Blockade of E-selectin may also reduce the metastatic potential of tumour types which carry the natural ligands for E-selectin, namely the sialyl Lewis x and sialyl Lewis a antigens.

In a further aspect of the invention there is provided a pharmaceutical or veterinary composition comprising a compound of formula (I) together with a pharmaceutically or veterinarily acceptable excipient or carrier.

One or more compounds of general formula (I) may be present in the composition together with one or more excipient or carrier.

The compounds with which the invention is concerned may be prepared for administration by any route which is compatible with the bioavailability of the compound in question. Thus, where the compound is bioavailable by the oral route, the compositions may be in the form of tablets, capsules, powders, granules, lozenges, liquid or gel preparations, such as oral, topical, or sterile parenteral solutions or suspensions. Tablets and capsules for oral administration may be in unit dose presentation form, and may contain conventional excipients such as binding agents, for example syrup, acacia, gelatin, sorbitol, tragacanth, or polyvinylpyrollidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulphate. The tablets may be coated according to methods well known in normal pharmaceutical practise. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

The dosage unit involved in oral administration may contain from about 1 to 250 mg, preferably from about 25 to 250 mg of a compound of general formula I. A suitable daily dose for a mammal may vary widely depending on the condition of the patient. However, a dose of a compound of general formula I of about 1 to 300 mg/kg body weight, particularly from about 10 to 100 mg/kg body weight may be appropriate.

For compounds which are absorbed by topical application to the skin, the drug may be made up into a cream, lotion or ointment. Cream or ointment formulations which may be used for the drug are conventional formulations well known in the art, for example as described in standard textbooks of pharmaceutics such as the British Pharmacopoeia.

The dosage for topical administration will of course depend on the size of the area being treated. For the eyes, each dose may typically be in the range from 10 to 100 mg of the drug.

The active ingredient may also be administered parenterally in a sterile medium.

Depending on the vehicle and concentration used, the drug can either be suspended or dissolved in the vehicle. Advantageously, adjuvants such as a local anaesthetic, preservative and buffering agents can be dissolved in the vehicle.

For use in the treatment of rheumatoid arthritis, the drug can be administered by the oral route or by injection intra-articularly into the affected joint. The daily dosage for a 70 kg mammal may be in the range 10 mgs to 1 gram.

EXAMPLES

The following examples 1–18 illustrate the preparation of compounds in accordance with the invention. Example 19 illustrates the preparation of starting materials for the preparation of further compounds in accordance with the invention. The biological example 20 illustrates the biological activity of compounds in accordance with the invention. All of the examples are by way of illustration only, and are not intended to limit the scope of the invention.

EXPERIMENTAL SECTION

General procedures

All solvents and reagents used were analar grade. Tetrahydrofuran was dried by heating under reflux in a still containing sodium metal and benzophenone for several hours under argon. Anhydrous THF was distilled immediately prior to use. Anhydrous dichloromethane was obtained from Aldrich. Solution transfers, where anhydrous conditions were required, were performed under argon using hypodermic syringes and cannulas. T.l.c. were performed on precoated silica gel plate 60-F254 plates (E. Merck, Darmstadt) and visualised by quenching of the fluorescence and (or) by charring after spraying with 5% anisaldehyde-5% sulphuric acid in ethanol. For "silica gel chromatography" 40–63 μM silica gel 60 was used, and the ratio of compound to silica was typically 1:30. Solutions of crude products in organic solvents were dried over $MgSO_4$. The organic solvents were removed on a rotary evaporator equipped with a dry-ice acetone condenser at bath temperatures below 40° C. under the vacuum of an oil pump. $^1$H nmr spectra were recorded at 250 MHz on a Bruker AM-250 with tetramethyl silane as an internal standard. $^{13}$C nmr spectra were recorded at 62.8 MHz with tetramethyl silane as an internal standard.

The nmr assignments are annotated as follows; S stands for the sialic acid residue, F for the fucose residue and L for the linker joining the two sugars. The number following the letter represents the atom's position within each of the sugar residues. The numbering system for the linker runs away from the fucose residue, hence L-1 for example, refers to the methylene adjacent to the 4-position of the fucose ring.

Low resolution mass spectra were performed on a ZAB1F mass spectrometer.

Example 1

1.1: α-O-Methyl-2,3-di-O-benzoyl-4-oxo-L-fucopyranoside (E1)

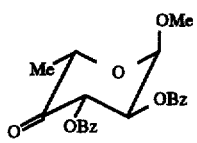

A suspension of α-O-Methyl-2,3-di-O-benzoyl-L-fucopyranoside (prepared by the method of Thiem et al, Carb. Res., 1991, 209, 113) (10.1 g, 26.2 mmol), pyridinium chlorochromate (25.4 g, 117.9 mmol) and dried powdered 4A sieves (50 g) was mechanically stirred in degassed anhydrous dichloromethane (400 ml) under argon at room temperature for 18 hr. The supernatant was decanted from the solids and the solids were triturated with 5 portions of dichloromethane (5×50 ml). The combined dichloromethane layers were passed through a short silica column and evaporated to give pure α-O-methyl-2,3-di-O-benzoyl-4-oxo-L-fucopyranoside as a colourless oil (E1) (8.01 g, 20.9 mmol, 80% yield).

$^1$H nmr: (CDCl$_3$) δ 8.05 (4H, 2d, OBz); 7.55 (2H, 2d, OBz); 7.5–7.35 (4H, 21, OBz); 6.16 (H, d, H-3); 5.58 (H, d, H-2); 5.28 (H, d, H-1); 4.48 (H, q, H-5); 3.56 (3H, s, OCH$_3$); 1.41 (3H, d, H$_3$-6).

$^{13}$C nmr: (CDCl$_3$) δ 197.7 (C-4), 165.5 (OCOPh), 133.5, 133.4, 130.0, 129.9, 129.0, 128.5, 128.5, 128.2 (2×OBz), 97.1 (C-1), 74.4, 72.8, 69.3, 56.2 (OCH$_3$), 13.8 (C-6).

1.2: α-O-Methyl-2,3-di-O-benzoyl-4R-hydroxy-4-(3'-dimethylphosphono-2'-oxo-propyl)-L-fucopyranoside (E2)

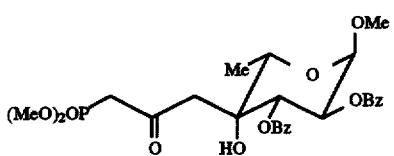

Dimethyl-2-oxopropylphoshonate (0.42 g) was added to a stirred suspension of hexane-washed NaH (97 mg) in dry tetrahydrofuran (10 ml) at room temperature under argon. After 10 minutes n-butyl lithium (3 ml of a 1.35M solution in hexanes, 2.53 mmol) was added to the stirred white slurry at 0° C. to give a deep yellow solution. After 30 minutes at 0° C., the solution was cooled to −78° C. and chlorotriisopropxy titanium (0.3 ml) was added from a warmed syringe. The dark brown solution was stirred for 5 minutes before a solution of E1 (214 mg) in tetrahydrofuran (5 ml) was added by syringe. The reaction mixture was stirred at −78° C. for 2 hr then quenched with 2M HCl (aq) (5 ml) and extracted twice with ethyl acetate (2×50 ml). The combined organic layers were dried and evaporated to give an oil. Flash chromatography on silica using a gradient eluant; ethyl acetate then 5% methanol-ethyl acetate gave the product contaminated with dimethyl-2-oxopropylphoshonate. This was removed by partial Kugelrohr distillation at 125° C. and 0.9 mm Hg to afford pure α-O-Methyl-2,3-di-O-benzoyl-4R-hydroxy-4-(3'-dimethylphosphono-2'-oxo-propyl)-L-fucopyranoside (E2) (125 mg 41% yield) as a light brown oil.

$^1$H nmr: (CDCl$_3$) δ 7.99–7.87 (4H, 2d, 2×OBz); 7.52–7.26 (6H, m, 2×OBz); 5.82(H, d,J=10.2 Hz, H-3); 5.49 (H, dd, J=3.8 and 10.2 Hz, H-2); 5.14 (H, d, J=3.8 Hz, H-1); 4.24 (H, q, J=6.4 Hz, H-5); 4.10 (H, br s, OH); 3.71 (3H, d, J=11.3 Hz, MeOP); 3.64 (3H, d, J=11.3 Hz, MeOP); 3.41 (3H, s, F1-OMe); 3.10–2.99 (2H, dd, J=5.5 and 22.6 Hz, (MeO)$_2$OPCH$_2$CO—); 2.86 (2H, s, COCH$_2$C-4); 1.30 (3H, d, J=6.4 Hz).

$^{13}$C nmr: (CDCl$_3$) δ 200.6 (—CCO—), 166.2, 166.0 (2×O COPh), 133.3, 133.3, 129.8, 129.7, 129.3, 129.2, 128.4, 128.2 (2×Ph); 97.0 (C-1), 75.1 (C-4), 72.9, 70.6, 67.8, 60.3 Cl-OCH$_3$), 53.0, 52.9 (P(OCH$_3$)$_2$), 46.8 (COCH$_2$C-4), 43.58 and 41.6 (PCH$_2$CO), 13.5 (C-6).

1.3: Methyl α-O-allyl-tetra-O-acetyl-N-acetyl-neuraminidate (E3)

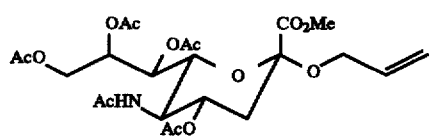

A suspension of silver salicylate (0.46 g, 1.87 mmol), freshly activated powdered 4A sieves (2.0 g) and methyl 13-chloro-tetra-O-acetyl-N-acetyl-neuraminidate (1.0 g, 1.87 mmol) (prepared by the method of Laferriere C. A. and Roy R., Can. J. Chem., 1990, 68, 2045) was stirred in allyl alcohol (6.7 ml) at room temperature under argon for 5 hr. The crude mixture was filtered through a pad of celite with dichloromethane (2×50 ml) and evaporated. The residue was taken up in chloroform (100 ml), washed twice with 2M sodium bicarbonate solution (2×20 ml) and twice with 5% sodium thiosulphate solution (2×10 ml) then dried over magnesium sulphate. Evaporation gave pure methyl α-O-allyl-tetra-O-acetyl-N-acetyl-neuraminidate (E3) as a white foam (0.97 g, 1.81 mmol, 93% yield).

$^1$H nmr: (CDCl$_3$) δ 5.83 (H, dddd, J=10.5, 7, 5, and 5 Hz, allyl —CH=); 5.35 (H, m, S-8); 5.30 (H, dd, J=8.5 and 1.8 Hz, S-7); 5.26 (H, dd, J=17.0 and 1.5 Hz, =CH$_2$); 5.14 (H, d, J=10 Hz, NHAc); 5.13 (H, dd, J=10.5 and 1.5 Hz); 4.83 (H, m, S-4); 4.27 (H, dd, J=12.5 and 2.7 Hz, S-9); 4.27 (H, m); 4.03–4.11 (3H, m); 3.84 CH, dd, J=12.5 and 5.8 Hz, S-9); 3.76 (3H, s, methyl ester); 2.59 (H, dd, 12.0 and 4.8 Hz, S-3e); 1.86, 2.0, 2.02, 2.11, 2.13 (15H, 5×s, NHAc and OAc).

$^{13}$C nmr: (CDCl$_3$) δ 171.2, 170.9, 170.4, 170.3, 168.5 (S-1), 133.6, 117.4, 98.2 (S-2), 72.5 (S-6), 69.0, 68.5, 67.3, 66.0, 62.3, 49.3, 38.0, 23.1, 21.0, 20.7, 20.6, 20.6.

1.4: Methyl α-O-(2'-oxoethyl)-tetra-O-acetyl-N-acetyl-neuraminidate (E4)

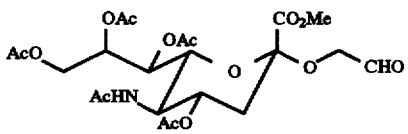

E3 (0.42 g, 0.78 mmol) was ozonolysed in dichloromethane-methanol (50 ml, 10 ml) at 0° C. for 2 hr. Methyl sulphide (2 ml) was added and the reaction mixture was stood for 8 hr at room temperature before evaporating. The residue was chromatographed on silica, eluant ethyl acetate to give methyl-α-O-(2'-oxoethyl)-tetra-O-acetyl-N-acetyl-neuraminidate (E4) as a white foam (0.28 g, 0.52 mmol, 66% yield).

$^1$H nmr: (CDCl$_3$) δ 9.58 (H, s, CHO); 5.62 (H, m); 5.28 (2H,m); 4.89 (H,m); 4.37–3.96 (6H, m); 3.77 (3H, s, OMe);

2.66 (H, dd, H-3e); 2.08 (6H, 2s, 2×OAc); 2.05 (H, dd, H-3a); 1.98 (6H, 2s, 2×OAc); 1.84 (3H,s, NHAc).

$^{13}$C nmr: (CDCl$_3$) δ 198.7 (CHO), 170.8, 170.6, 170.5, 170.0, 167.8, 98.4 (C-2), 72.6, 69.9, 68.8, 68.2, 67.0, 62.3, 60.4, 53.0, 49.2, 37.5, 23.0 (NHCOCH$_3$), 21.0, 3×20.7.

1.5: Structures of E5 and E15

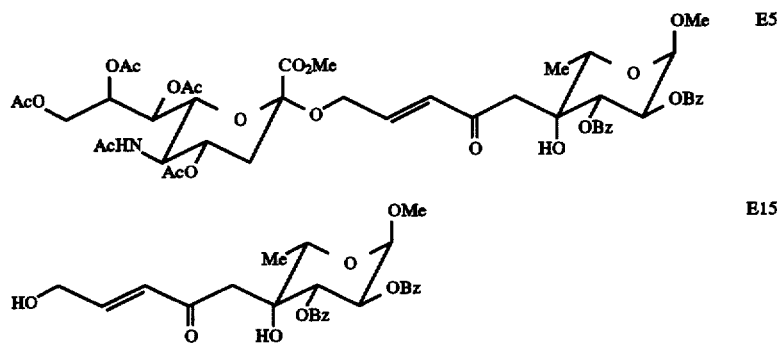

α-O-Methyl-2,3-di-O-benzoyl-4R-[{tetra-O-acetyl-N-acetyl-α2"-O-neuraminidyl methyl ester}5'-oxy-2'-oxo-pent-3'-en-1'-yl]-L-fucopyranoside (E5)

and

α-O-Methyl-2,3-di-O-benzoyl-4R-[5'-hydroxy-2'-oxo-pent-3'-en-1'-yl]-L-fucopyranoside (E15)

A suspension of caesium carbonate (180 mg, 0.65 mmol), E2 (300 mg, 0.55 mmol) and E4 (300 mg, 0.56 mmol) was stirred in 2-methyl-propan-2-ol (10 ml) for 2 hr at 30° C. The yellow solution was quenched with 2M H$_3$PO$_4$ (aq) (1 ml) and evaporated in vacuo. The residue was taken up in dichloromethane (80 ml), washed with sodium bicarbonate solution (20 ml) and water (20 ml) then dried over magnesium sulphate and concentrated. The crude reaction mixture was flash chromatographed on silica using ethyl acetate to afford α-O-methyl-2,3-di-O-benzoyl-4R-hydroxy-4-1'-[α2"-O-{methyl tetra-O-acetyl-N-acetyl-neuraminidate-yl}5'-oxy-2'-oxo-pent-3'-enyl]-L-fucopyranoside (E5) as a white foam (320 mg, 0.33 mmol, 60% yield). The allylic alcohol (E15) was also isolated as an oil (21 mg)

Spectral data on disaccharide enone (E5)

$^1$H nmr: (CDCl$_3$) δ 7.9 (4H, m, OBz); 7.5–7.3 (6H, m, OBz); 6.57 (H, dt, L-4); 6.15 (H, d, L-3); 5.82 (H, d, F-3); 5.50 (H, dd, F-2); 5.3 (2H, m, S-7, S-8); 5.15 (H, d, F-1); 4.85 (2H, m, S-4, NH); 4.33–3.85 (6H, m, 2×L-5, 2×S-9, F-5, S-6); 3.77 (H, br s, OH); 3.75 (3H, s, F-OMe); 2.85 (H, d, L-1); 2.65 (H, d, L-1'); 2.57 (H, dd, S3e); 2.15 (6H, 2xs, 2×OAc); 2.10 (H, m, S3a); 2.05 (6H, 2×s, 2×OAc); 1.90 (3H, s, NHAc); 1.30 (3H, d, F-6).

$^{13}$C nmr: (CDCl$_3$) δ 199.3 (L-2), 170.8, 170.5, 170.2, 170.0, 169.9, 167.9, 166.0, 165.9, (4×OAc, NHAc, 2×OBz, S-1), 143.4 (L-4), 2×133.1, 129.7, 129.4, 129.4, 128.2, 128.2 (2×OBz), 128.3 (L-3), 98.3 (S-2), 97.0 (F-1), 75.9 (F-4), 73.1 (F-3), 72.5 (F-5), 70.8 (F-2), 68.8 (S-4), 68.6 (S-6), 68.3 (S-8), 67.2 (S-7), 63.2 (S-9), 62.4 (L-5), 55.4 (F-O Me), 52.8 (S-OMe), 49.3 (S-5), 42.2 (L-1), 37.7 (S-3), 23.0 (NHAc), 21.0, 20.7, 20.7, 20.6 (4×OAc), 13.9 (F-6).

m/z

Spectral data on allylic alcohol (E15)

$^1$H nmr: (CDCl$_3$) δ 8.0–7.88 (4H, m, 2×OBz); 7.53–7.27 (6H, m, 2×OBz); 6.67 (H, dt, J=15.8 and 3.8 Hz, L4); 6.15 (H, dt, J=15.8 and 1.9 Hz, L3); 5.82 (H, d, J=10.3 Hz, F3); 5.47 (H, dd, J=10.3 and 3.8 Hz, F2); 5.18 (H, d, J=3.8 Hz); 4.90 (H, br s, OH); 4.12 (3H, m, L5, F5); 3.41 (3H, s, F1-OMe); 2.85 (H, d, J=15.6 Hz, L1); 2.57 (H, d, J=15.6 Hz, L1'); 1.33 (3H, d, J=6.4 Hz, F6).

Example 2

αO-Methyl-2,3-di-O-benzoyl-4R-[{tetra-O-acetyl-N-acetyl-α2"-neuraminidyl methyl ester}5'-oxy-2'-oxo-pent-1'-yl]-L-fucopyranoside (E6)

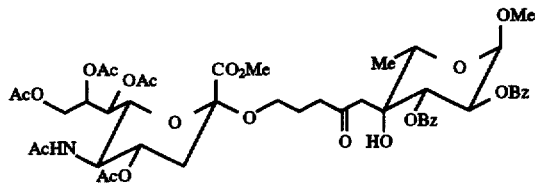

E5 (70 mg, 7.31×10$^{-5}$M) was stirred with 10% palladium on charcoal (5 mg) in methanol (5 ml) at room temperature under 1 atm of hydrogen gas. After 16 hr the reaction mixture was filtered through a pad of celite and concentrated to afford α-O-methyl-2,3-di-O-benzoyl-4R-[{α-methyl-tetra-O-acetyl-5"N-acetyl-neuraminidate-2"-yl}5'-oxy-2'-oxo-pent-1'-yl]-L-fucopyranoside (E6) as a yellow foam (68 mg, 7.10×10$^{-5}$M, 98%).

$^1$H nmr: (CDCl$_3$) δ 7.97–7.87 (4H, 2×d, OBz); 7.52–7.27 (6H, m, OBz); 5.76 (H, d, J=10.3 Hz, F-3); 5.51 (H, dd, J=10.3 and 3.6 Hz, F-2); 5.35–5.23 (3H, m, S-7, S-8, OH); 5.14 (H, d, J=3.6 Hz, F-1); 4.86 (H, br s, NH); 4.82 (H, m, S-4); 4.30 (H, dd, J=1.9 and 12.2 Hz); 4.15–4.02 (3H, m, S-9', S-6, F-5); 3.79 (3H, s, S-OMe); 3.59 (H, m, L-5); 3.41 (3H, s, F-OMe); 3.13 (H, m, L-5"); 2.63 (2H, 4 lines, J=10.3 Hz, L-1, L-1'); 2.50 (H, dd, J=4.6 and 12.9 Hz, S-3e); 2.42 (2H, q, J=7.3 Hz, L-3); 2.13 (3H, s, OAc); 2.12 (3H, s, OAc); 2.07 (H, S-3a); 2.02 (3H, s, NHAc); 1.5 (2H, m, L-4); 1.29 (3H, d, J=6.3 Hz, F-6).

$^{13}$C nmr: (CDCl$_3$) δ 210.5 (L-2), 170.9–165.9 8 lines (4×OAc, 2×OBz, CO$_2$Me, NHAc), 133.3, 133.0, 129.8, 129.7, 129.3, 129.1, 128.4, 128.2 (2×OBz), 98.6, (S-2), 97.1 (F-1), 75.6 (F-4), 73.4 (F-3), 72.5 (F-5), 70.6 (F-2), 69.1, 68.6, 68.3, 67.3 (S-4, S-6, S-7, S-8), 63.5 (S-9), 62.4 (L-5), 55.5 (F-OMe), 52.6 (S-OMe), 49.3 (S-5), 44.5 (L-1), 40.7 (L-3), 37.9 (S-3), 23.1 (NHAc), 22.1 (L-4), 21.0, 20.8, 20.8, 20.7 (4×OAc), 13.8 (F-6).

Example 3

α-O-Methyl-4R-[{5"N-acetyl-α2"-O-neuraminidyl methyl ester}-5'-oxy-2'-oxo-pent-1'-yl]-L-fucopyranoside (E7)

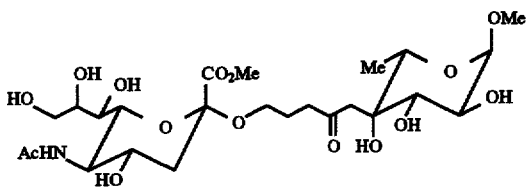

E6 (50 mg, 5.21×10$^{-5}$M) was stirred with 1 equivalent (5.0×10$^{-5}$M) of sodium methoxide in anhydrous methanol (4 ml) under argon for 14 hr. The reaction mixture was neutralised with 1 drop of hydrochloric acid then concentrated and flash chromatographed on silica using a gradient elution of 10% increasing to 50% methanol in ethyl acetate. O-Methyl-4R-[{5"N-acetyl-α2"-neuraminidyl methyl ester}5'-oxy-2'-oxo-pent-1'-yl]-L-fucopyranoside (E7) was obtained as a light yellow oil (20 mg, 66% yield).

$^1$H nmr: (D$_2$O) δ 4.84 (H, d, F-1); 4.07 (H, q, J=6.4 Hz, F-5); 3.83 (3H, s, S-OMe); 3.82– 3.39 (11H, m, F-2, F-3, S-4, S-5, S-6, S-7, S-8, 2×S-9, 2×L-5); 3.36 (3H, s, F-OMe); 2.87 (H, d, J=16.4 Hz, L-1); 2.66–2.59 (4H, m, L-1', 2×L-3, S-3e); 1.99 (3H, s, NHAc); 1.87–1.70 (3H, m, 2×L-4, S-3a); 1.12 (3H, d, J=6.4 Hz, F-6).

$^{13}$C nmr: (D$_2$O) δ 213.5 (L-2), 175.2 (S-1), 178.4 (NHAc), 99.5 (S-2), 99.4 (F-1), 76.0 (F-4), 73.1 (S-8), 71.3 (F-2), 70.9 (F-3), 69.2 (S-7), 68.5 (S-6), 68.1 (F-5), 67.4 (S-4), 64.1 (L-5), 63.3 (S-9), 55.3 (F-OMe), 53.6 (S-OMe), 52.0 (S-5), 45.5 (L-1), 40.6 (L-3), 39.4 (S-3), 23.2 (L-4), 22.3 (NHAc), 13.0 (F-6).

Example 4

α-O-Methyl-4R-[{N-acetyl-α2"-neuraminidyl sodium carboxylate}5'-oxy-2'-oxo-pent-1'-yl]-L-fucopyranoside (E8)

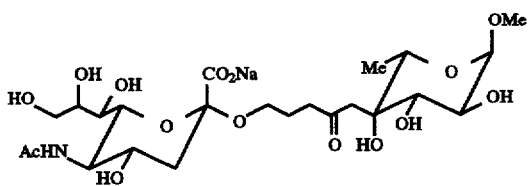

E7 (15 mg, 2.56×10$^{-5}$M) was dissolved in D$_2$O (0.6 ml) containing one equivalent of sodium deuteroxide (2.6×10$^{-5}$M). Saponification as judged by 1H nmr was complete after 18 hr. The solution was concentrated to give αO-Methyl-4R-[{N-acetyl-α2"-O-neuraminidyl sodium carboxylate}5'-oxy-2'-oxo-pent-1'-yl]-L-fucopyranoside (E8) as a clear glass (17 mg, quantitative yield).

$^1$H nmr: (D$_2$O) δ 4.8 (H, d, F-1); 4.08 (H, q, F-5); 3.9–3.39 (10H, m); 3.35 (3H, s, FOMe); 2.68 (H, dd, S-3e); 2.04 (3H, s, NHAc); 1.8–1.3 (5H, m, 2×L-1, 2×L-3, 2×L-4, S-3a); 1.18 (3H, d, F-6).

$^{13}$C nmr: (D$_2$O) δ 181.3, 175.4, 173.8, 100.8, 99.5, 76, 74.6, 72.8, 72.0, 69.3, 68.5, 68.3, 64.0, 62.9, 55.3, 52.3, 49.0, 40.7, 23.6, 23.2, 22.3, 13.1.

Example 5

α-O-Methyl-2,3-di-O-benzoyl-4R-[{tetra-O-acetyl-5"N-acetyl-α2"-neuraminidyl methyl ester}5'-oxy-2'(R and S)-hydroxy-pent-3'-en-1'-yl]-L-fucopyranoside (E9)

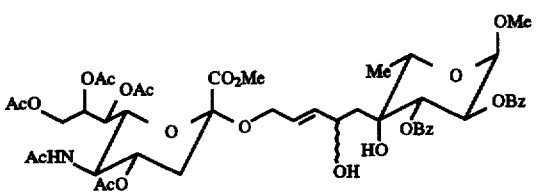

Sodium borohydride (26 mg, 6.9×10$^{-4}$M) was added bit by bit to a stirred solution of E5 (220 mg, 2.30×10$^{-4}$M) and CeCl$_3$nH$_2$O (85 mg, 3.45×10$^{-4}$M in methanol (5 ml) at room temperature. After 1 hr the reaction mixture was quenched with 2M H$_3$PO$_4$ (aq) (3 ml) and concentrated in vacuo. The residue was partitioned between dichloromethane (50 ml) and 2M HCl (aq) (50 ml) and then the organic layer was dried over magnesium sulphate and evaporated to afford αO-methyl-2,3-di-O-benzoyl-4R-[{tetra-O-acetyl-N-acetyl-α2"-O-neuraminidyl methyl ester}5'-oxy-2'(R and S)-hydroxy-pent-3'-en-1'-yl]-L-fucopyranoside (E9) as a white foam (170 mg, 1.77×10$^{-4}$M, 77% yield). The ratio of epimers at L-2 is approximately 3:2 by $^1$H nmr.

$^1$H nmr: (CDCl$_3$) δ 8.00–7.87 (4H, m, OBz); 7.47–7.27 (6H, m, OBz); 5.90 (½H, d); 5.75 (½H, d): 5.64–5.24 (6H, m, ); 5.13 (H, m, F-1); 4.81 (H, m, 4.51–3.93 (9H, m); 3.85–3.72 (H,m); 3.71 and 3.65 (3H, 2×s, S-OMe); 3.39 (3H, s, FOMe); 2.54 (H, S-3e); 2.09, 2.03–1.99 and 1.92 (13H, 8×s, 4×OAc, S-3a); 1.84 (3H, 2×s, NHAc); 1.77–1.6 (H, m, L-1); 1.37–1.29 (H, m, L-1'); 1.25 and 1.22 (3H, 2×d, F-6).

$^{13}$C nmr: (CDCl$_3$) δ 171.0, 170.9, 170.2, 168.4, 166.0, 135.2, 134.9, 133.0, 129.7, 129.3, 128.6, 126.0, 98.4 (2 lines S-2), 97.0 (F-1), 75.3, 73.9, 72.6, 72.3, 71.3, 70.9, 69.3, 69.1, 68.5, 67.5, 64.6, 62.9 (CH$_2$), 62.4 (CH$_2$), 55.4, 52.8, 49.1, 40.0 (CH$_2$), 37.8 (CH$_2$), 23.2, 21.1, 20.9, 20.8, 14.1, 13.8. (not all lines entered).

Example 6

α-O-Methyl-4R-[{5"N-acetyl-α2"-neuraminidyl methyl ester}5'-oxy-2'(R and S)-hydroxy-pent-3'-en-1'-yl]-L-fucopyranoside (E10)

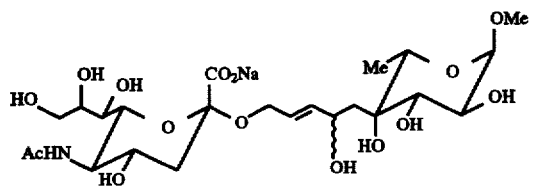

E9 (92 mg, 9.6×10$^{-5}$M) was stirred with two equivalents of sodium methoxide (1.8×10$^{-4}$M) in methanol (5 ml) at room temperature under argon. After 16 hr the reaction mixture was neutralised with Dowex H$^+$ resin and preabsorbed onto silica (0.5 g). Flash chromatography on silica using a gradient elution of 10% rising to 50% methanol-ethyl acetate gave α-O-Methyl-4R-[{5"N-acetyl-α2"-neuraminidyl methyl ester}5'-oxy-2'(R and S)-hydroxy-pent-3'-en-1'-yl]-L-fucopyranoside (E10) as a white solid (32 mg, 5.5×10$^{-5}$M, 57% yield). The ratio of epimers is approximately 2:1.

$^1$H nmr: (CD$_3$OD) δ 5.69 (2H, m, L-3, L-4); 4.78 (3H,m); 4.60 (H, d, F-1); 4.28–4.22 (2H, m); 3.93 (2H, m); 3.80 (3H, s, S-OMe); 3.82–3.45 (7H, m); 3.33 (3H, s, F-OMe); 2.65 (H, dd, J=4.3 and 12.7 Hz, S-3e); 1.97 (3H, s, NHAc); 1.89–1.66 (2H, m, S-3a, L-1); 1.56–1.46 (H, m, S-1'); 1.15 and 1.14 (3H, 2×d, J6.3 Hz, F-6).

$^{13}$C nmr: (CD$_3$OD) δ 175.2 (S-1), 171.0, 137.5 and 137.3 (L-3), 126.9 and 126.7 (L-4), 101.1 (F-1), 100.1 (S-2), 76.3 (F-4), 75.0, 73.7, 72.8, 72.4, 71.0, 70.2, 69.9, 69.7, 69.0, 68.5, 68.4, 65.4 (2 lines L-5), 64.7 (S-9), 55.6 (S-OMe), 53.8 and 53.5 (S-5 and F-OMe), 43.3 and 42.5 (L-1), 41.7 (S-3), 22.7 (NHAc), 14.3 and 14.0 (F-6).

m/z

Example 7

α-O-Methyl-4R-[{acetyl-α2"-neuraminidyl sodium carboxylate}5'-oxy-2'(R and S)-hydroxy-pent-3'-en-1'-yl]-L-fucopyranoside (E11)

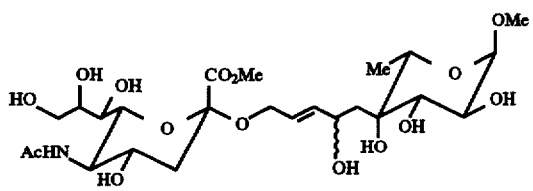

E10 (17 mg, 2.9×10$^{-5}$M) was stirred with two equivalents of NaOD (5.81×10$^{-5}$M) in D$_2$O (0.5 ml) for 20 hr. The reaction mixture was concentrated in vacuo to give the desired sodium carboxylate salts (E11) (17 mg, quantitative yield).

$^1$H nmr: (D$_2$O) δ 5.74 (2H, m, L-3, L-4); 4.9–4.7 (water peak obscuring F-1); 4.27 (2H, m); 4.05–3.90 (2H, m); 3.82–3.49 (9H, m); 3.34 (3H, s, F-OMe); 3.29 (4H, m); 2.66 (H, m); 1.98 (3H, s, NHAc); 1.98–1.89 (H, m, S-3a); 1.82–1.55 (2H, m, L1); 1.16 and 1.14 (3H, 2×d, F-6).

$^{13}$C nmr: (D$_2$O) δ 175.3 (S-1), 170.4 (NHAc), 136.6 and 136.4 (L-3), 126.5 and 126.1 (L-4), 99.3 (F-1 and S-2), 75.7 and 75.5 (F-4), 73.3, 73.0, 72.0, 71.4, 70.9, 70.7, 69.4, 68.6, 68.0, 67.6, 67.4, 65.0 (2 lines L-5), 63.4 and 62.9 (S-9), 55.3 (F-OMe), 53.7, 52.0, 49.2, 40.7 (S-3), 40.3 and 39.6 (L-1), 22.4 and 22.3 (NHAc), 13.2 and 12.9 (F-6).

Example 8

α-O-Methyl-2,3-di-O-benzoyl-4R-[{tetra-O-acetyl-N-acetyl-α2"-neuraminidyl methyl ester}5'-oxy-2'(R and S)-hydroxy-pent-1'-yl]-L-fucopyranoside (E12)

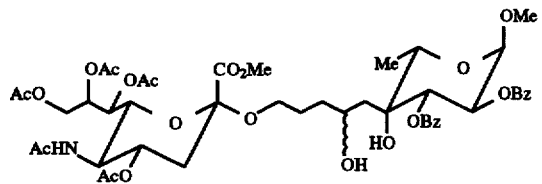

E9 (81 mg, 8.44×10$^{-5}$M) was stirred with 10% palladium on charcoal catalyst (10 mg) in methanol (5 ml) for 3 hr. The reaction mixture was filtered through celite using methanol (50 ml) and then evaporated to give the saturated alcohol (E12) as a white foam (82 mg, 100% yield).

$^1$H nmr δ (CDCl$_3$) 8.01–7.86 (4H, m); 7.46–7.26 (6H, m); 5.92 and 5.73 (H, 2×d, J=10.3 Hz and 10.2 Hz, F-3); 5.51–5.25 (4H, m); 5.14 (H, F-1); 4.82 (H, m); 4.32–3.6 (11H, m); 3.36 (3H, 2×s, F-OMe); 3.23 (H, m); 2.51 (H, m, S-3e); 2.11–1.84 (15H, 4×OAc and NHAc); 1.80–1.30 (10H, m).

$^{13}$C nmr δ (CDCl$_3$) 171.0–166.1 (7 lines), 133.3 (2 lines), 129.7, 129.3 128.4, 128.4, 128.2, 98.6 (2 lines, S-2), 97.0 (F-1), 75.3, 74.2, 72.4, 71.3 and 71.1, 69.5–67.4 (6 lines), 65.0, 62.7, 62.6, 55.4 (2 lines). 52.6, 49.2, 41.3, 40.1, 37.9, 35.5, 35.3, 25.5, 23.1, 21.0–20.8 (multiple lines), 13.7 and 13.5.

m/z

Example 9

α-O-Methyl-4R-[{N-acetyl-α2"-neuraminidyl carboxylic acid}5'-oxy-2'(R and S)-hydroxy-pent-1'-yl]-L-fucopyranoside (E13)

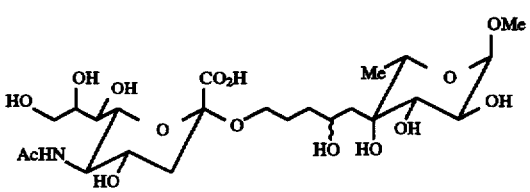

E12 (66 mg, 6.9×10$^{-5}$M) was stirred with two equivalents of sodium methoxide (1.4×10$^{-4}$M) in methanol (4 ml). After 14 hr the reaction mixture was neutralised with 2M HCl (aq) (0.1 ml) and azeotroped to dryness with toluene. The residue was taken up in methanol, preabsorbed onto silica and flash chromatographed on silica using a gradient elution of 10% methanol-ethyl acetate rising to neat methanol. The carboxylic acid (E13) was obtained as a white solid (38 mg, 6.65×10$^{-5}$M, 96% yield).

$^1$H nmr (D$_2$O) δ 4.9–4.8 (H$_2$O peak) 4.62 (H,m); 4.03 (H, q, J=6.9 Hz, F-5); 3.99–3.40 (13H, m); 3.31 (3H, s, F-OMe); 3.27 (3H, m); 2.78 (H, dd, J=3.6 and 12.5 Hz, S-3e); 1.98 (3H, s, NHAc); 1.82–1.35 (7H, m); 1.16 and 1.14 (3H, 2×d, J=6.9 Hz, F-6).

$^{13}$C nmr (CD$_3$OD) δ 175.5, 174.8 (2 lines), 101.8 (S-2), 101.1 and 101.0 (F-1), 76.6, 76.4, 74.3, 73.9, 72.9. 72.4, 71.0, 70.3, 69.7, 69.5, 69.3, 69.1, 67.4, 65.1 and 64.6 (L-5), 64.3 (S-9), 55.6 and 55.5 (F-OMe), 54.2 (S-5), 43.3, 42.8 and 42.6 (S3 and L-1), 36.7 and 36.3 (L-3), 26.8 and 26.7 (L-4), 22.7 (NHAc), 14.3 and 14.0 (F-6).

m/z

Example 10

α-O-Methyl-2,3-di-O-benzoyl-4R-[{tetra-O-acetyl-N-acetyl-α2"-neuraminidyl methyl ester}5'-oxy-2', 3',4'-trihydroxy-pent-1'-yl]-L-fucopyranoside (E14)

4 epimers synthesised (2'R, 3'R, 4'S), (2'S, 3'R, 4'S), (2'R, 3'S, 4'R) and (2'S, 3'S, 4'R)

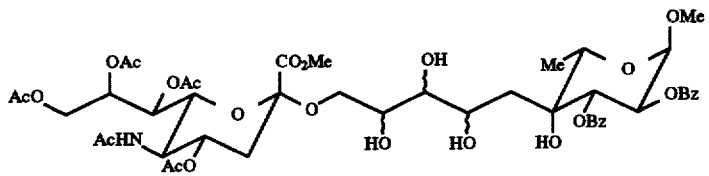

A solution of osmium tetroxide (2.5% by weight) in t-butanol (25 μl, 1.6×10⁻³M) was added to a solution of E9 (95 mg, 9.9×10⁻⁵M), t-butyl hydroperoxide (70% in $H_2O$) (22 μl, 1.6×10⁻⁴M) and tetraethyl ammonium acetate tetrahydrate (7 mg, 2.48×10⁻⁵M) in acetone (4 ml) and the mixture was stirred for 60 hr at room temperature. Water (5 ml), sodium bisulphite (0.5 g) and ethyl acetate (20 ml) were added, and stirring was continued for 20 min before the layers were separated. The aqueous phase extracted with ethyl acetate (20 ml) and the combined organic layers were dried over magnesium sulphate and evaporated to afford a yellow oil. Flash chromatography on silica using ethyl acetate gave an inseparable mixture of the diastereomeric triols (E14) as a white solid (40 mg, 4.0×10⁻⁵M).

¹H nmr: ($CDCl_3$) δ 8.0–7.82 (4H, m, OBz); 7.48–7.28 (6H, m, OBz); 6.00–5.78 (H, m); 5.62—5.09 (xH, m); 4.86 (H, m); 4.35–3.6 (xH, m); 3.34 (3H, 3×s, F-OMe); 2.6–2.55 (H, m, S-3e); 2.15–1.87 (15H, several singlets, 4×OAc, NHAc); 1.4–1.3 (5H, m).

Example 11

α-O-Methyl-4R-[{N-acetyl-α2"-neuraminidyl sodium carboxylate}5'-oxy-2',3',4'-trihydroxy-pent-1'-yl]-L-fucopyranoside (E16)

epimers synthesised (2'R, 3'R, 4'S), (2'S, 3'R, 4'S), (2'R, 3'S, 4'R), and (2'S, 3'S, 4'R)

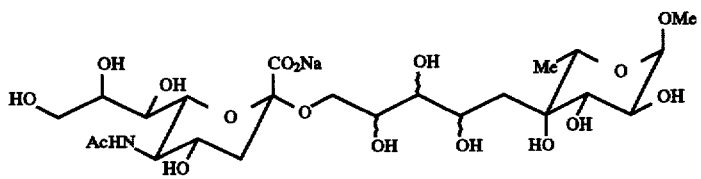

E15 (40 mg, 4.0×10–5M) was taken up in dry methanol (4 ml) containing one equivalent of sodium methoxide (4.0×10⁻⁵M). After 24 hr at room temperature, the reaction mixture was evaporated and the residue flash chromatographed on silica using a gradient elution of 20% rising to 50% methanol in ethyl acetate. The desired triol carboxylic acid sodium salts (E16) were obtained as an oil. (10 mg)

¹H nmr δ ($D_2O$) 4.9 (H, m, F-1), 4.1–3.4 (14H, m); 3.30 (3H, 3 lines, F-OMe); 2.6 (H, m, S-3e); 1.97 (3H, s, NHAc); 1.85 (H, m); 1.7–1.5 (2H, L-1); 1.15 (3H, m, F-6).

¹³C nmr δ ($D_2O$) 175.3, 174.0, 101.0. 100.8, 99.5, 99.46, 76.1, 75.8, 74.8–74.0 (5 lines), 73.0, 72.3–71.8 (3 lines), 69.8, 69.4, 69.2, 68.5, 68.0, 67.5, 66.7, 66.4, 63.0, 61.2, 55.2, 53.4, 52.6, 49.1, 40.9 (2 lines), 39.7, 39.2, 37.7, 22.3, 14.4, 13.4, 13.0.

Example 12

12.1: Methyl α2-O-(pent-4'-en-1'yl)-tetra-O-acetyl-N-acetyl-neuraminidate (E17)

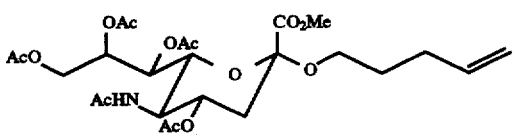

A suspension of methyl β-2-chloro-4,7,8,9-tetra-O-acetyl-5-N-acetyl-neuraminidate (375 mg, 0.74 mmol), silver salicylate (175 mg) and freshly activated powdered 4A sieves (250 mg) was stirred in dry 4-penten-1-ol (7.6 ml) at room temperature in the dark. The slurry was filtered through celite and washed well with dichloromethane. The filtrate was evaporated in vacuo, then the residue was redissolved in dichloromethane (20 ml) and washed with 5% $NaHCO_3$(aq), 5% sodium thiosulphate (aq), and water. Drying over magnesium sulphate and evaporation gave E17 as a white foam (330 mg, 0.59 mmol, 80% yield).

¹H nmr δ ($CDCl_3$) 1.8, 2.0, and 2.1 (15H, 5×s, 4×OAc, NHAc); 3.7 (3H, S-OMe); 4.9 (2H, m, $CH_2$=); 5.7 (H, m, —CH=).

¹³C nmr δ ($CDCl_3$) 20.6, 20.7, and 20.9 (4×AcO), 22.9 (NHAc), 29.8 and 29.9 (2×$CH_2$), 37.9 (S-3), 46.2 (S-5), 52.4 (OMe), 62.3 ($CH_2$), 64.0 (S-9), 67.4 (S-4), 68.3 and 69.0 (S-7 and S-8), 72.3 (S-6), 98.6 (S-2), 114.7 ($CH_2$=), 137.8 (—CH=), 168.4, 170.0, 170.5, 170.7, 170.7 and 170.8 (4×OAc, NHAc and S-2).

12.2: Methyl-α2-O-(4'-oxobutan-1'yl)-tetra-O-acetyl-N-acetyl-neuraminidate (E18)

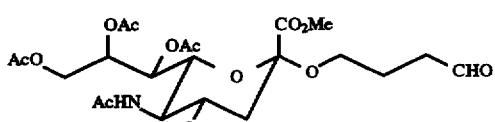

E17 (330 mg, 5.9×10⁻⁴M) was ozonolysed as described for E4 to give, after chromatography (silica/ethyl acetate), the desired aldehyde E18 as a white foam (210 mg, 3.7×10⁻⁴M, 63% yield).

¹H nmr δ ($CDCl_3$) 1.8 (5H, s, NHAc, $CH_2$); 2.0 (8H, 2×s+m, 2×OAc and $CH_2$); 2.1 (7H, 2×s+m, 2×OAc and S-3a); 2.5 (H, m, S-3e); 3.8 (5H,, m, S-OMe and OCH$_2$); 4.1 (2H, m, S-9); 4.3 (H, dd); 4.8 (H, m); 5.3 (2H, m); 5.5 (H, d, NH); 9.7 (H, s, CHO).

12.3: O-Methyl-2,3-di-O-benzoyl-4R-[{tetra-O-acetyl-N-acetyl-α2″-O-neuraminidyl methyl ester}7'-oxy-2'-oxo-hept-3'-en-1'-yl]-L-fucopyranoside (E19)

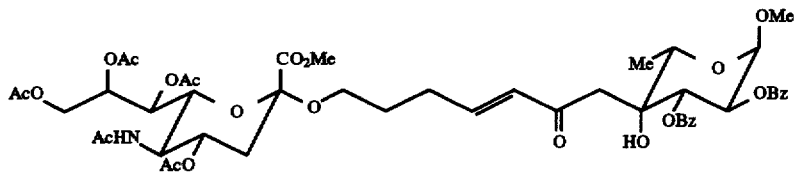

Caesium carbonate (72 mg, 2.1×10$^{-4}$M) was added to a stirred solution of E2 (100 mg, 1.8×10$^{-4}$M) and E18 (102 mg, 1.8×10$^{-4}$M) in t-butanol (12 ml) at room temperature. After 18 hr the reaction mixture was quenched with several drops of 6M HCl (aq) and toluene was added. The solvents were removed in vacuo to give an off-white foam. Chromatography on silica, eluant ethyl acetate gave enone E19 as a white foam (70 mg, 7.1×10$^{-5}$M, 48% yield).

$^1$H nmr δ (CDCl$_3$) 1.3 (3H, d, F-6); 1.8 (3H, s NHAc); 2.0 (6H, 2×s, OAc); 2.1 (6H, 2×s, OAc); 3.4 (3H, s, F-OMe); 5.8 (H, d, L-3); 6.7 (H, dt, L-4); 7.0–7.5).

$^{13}$C nmr δ (CDCl$_3$) 13.9 (F-6). 20.7, 20.8, 21.0, 23.1 (NHAc), 27.5, 28.7, 38.0 (S-3), 41.1, 49.3 (S-5), 52.6 (S-OMe), 55.4 (F-OMe), 62.3 (L-7), 63.7 (S-9), 67.3, 68.4, 68.9, 69.0, 71.0, 72.4, 73.2, 97.0 (F-1), 98.6 (S-2), 128–130, 132.9, 133 (L-4), 149.7 (L-3), 165.9, 168.3, 170.0, 170.3, 170.6, 170.9, 200.2 (L-2).

m/z FAB (ex PTTDTE NaOAc/MCA) 1008 MNa$^+$

Example 13

α-O-Methyl-2,3-di-O-benzoyl-4R-[{tetra-O-acetyl-N-acetyl-α2″-neuraminidyl methyl ester}7'-oxy-2'R and S-hydroxy-hept-3'-en-1'-yl]-L-fucopyranoside (E20)

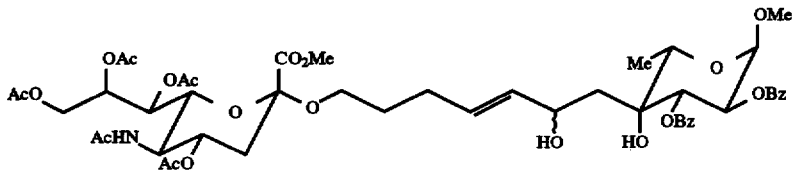

E19 (50 mg, 5.08×10$^{-5}$M) and cerium trichloride (19 mg, 7.61×10$^{-5}$M) were stirred for min in ethanol (5 ml) then sodium borohydride (6 mg, 1.52×10$^{-4}$M) was added. After 20 min, more sodium borohydride (100 mg) was added and the reaction mixture was stirred for 5 min. before quenching with 2M HCl (aq). The solvent was removed in vacuo and the residue taken up in ethyl acetate (50 ml), washed with 2M HCl (aq) (50 ml), dried over magnesium sulphate and evaporated to give the alcohols E20 as a yellow oil (50 mg). The epimer ratio (a:b) was 3:7.

$^1$H nmr δ (CDCl$_3$) 7.97–7.87 (4H, m, 2×OBz); 7.46–7.27 (6H, m, 2×OBz); 5.945 (³⁄₁₀H, d, J=10.4 Hz, F$_a$-3); 5.68 (⁷⁄₁₀H, d, J=9.5 Hz, F$_b$-3); 5.4–5.3 (6H, m, F-2, S-7, S-8, S-4, L-3, L-4); 5.16 (H, d, J=4.3 Hz, F-1); 4.5–3.70 (14H, m); 3.41 (3H, s, F-OMe); 2.6 (H, m, S-3e); 2.1–2.0 (15H, m, 4×OAc and NHAc); 2.0–1.35 (7H, m); 1.27 and 1.24 (3H, 2×d, J=7.0 Hz).

Example 14

α-O-Methyl-4R-[{N-acetyl-α2″-neuraminidyl methyl}7'-oxy-2'R and S-hydroxy-hept-3'-en-1'-yl]-L-fucopyranoside (E21)

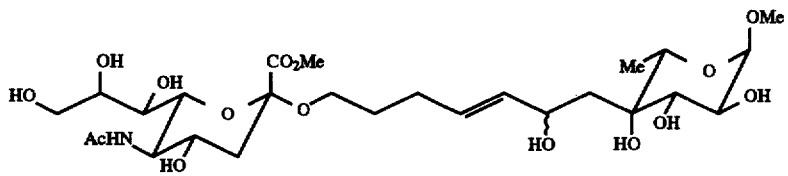

E20 (50 mg) was treated with two equivalents of sodium methoxide ($1.1 \times 10^{-4}$M) in dry methanol (4 ml) at room temperature for 20 hr. The solution was preabsorbed and flash chromatogaphed on silica using a gradient elution of 20% rising to 50% methanol-ethyl acetate to give the methyl esters E21 as a yellow oil (19 mg, $3.1 \times 10^{-5}$M, 62% yield from E19).

$^1$H nmr δ (CD$_3$OD) 5.67–5.37 (2H, m, L3, L-4); 4.58 (H, d, F-1); 4.32–4.20 (H, m, S-5); 3.94 (H, q, F-5); 3.87–3.28 (15H, m including 3 singlets at 3.68 3.33 and 3.31: these are S-OMe and 2xF-OMe); 2.64 (H, dd, J=4.6 and 12.8 Hz, S-3e); 2.05–1.43 (10H, m including s at 1.97, NHAc, S-3a, 2xL-1, 2xL-5, 2xL-6); 1.16 and 1.13 (3H, 2xd, F-6).

$^{13}$C nmr δ (CD$_3$OD) 175.2, 171.2, 135.3, 131.3, 130.9, 101.2, 101.1,100.6, 76.2, 74.9, 73.6, 72.5, 71.1, 70.2, 69.6, 69.3, 69.0, 68.5, 64.7, 64.4, 55.5, 53.8, 53.4, 43.5, 41.7, 30.2, 29.4, 22.6, 22.6, 14.2, 13.9.

m/z

Example 15

α-O-Methyl-4R-[{N-acetyl-α2"-neuraminidyl sodium carboxylate}7'-oxy-2'R and S-hydroxy-hept-3'-en-1'-yl]-L-fucopyranoside (E22)

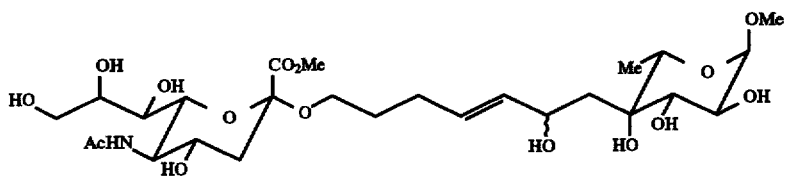

E21 was hydrolysed using two equivalents of NaOD in D$_2$O affording the sodium carboxylate salts E22 as an oil (19 mg, $3.1 \times 10^{-5}$M, quantitative yield).

$^1$H nmr δ (D$_2$O) 5.50–5.46 (2H, m, L-3, L-4); 4.92 (H, m, F-1); 4.19 (H, m); 3.98 (H, m); 3.82 (H, m); 3.82–3.35 (12H, m); 3.30 (3H, s, F-OMe); 2.67 (H, m, S-3e); 2.08–2.02 (3H, m); 1.98 (3H, s, NHAc); 1.64–1.59 (4H, m); 1.17 and 1.14 (3H, 2xd, 6.6 and 6.6 Hz, F-6).

$^{13}$C nmr δ (D$_2$O) 175.3, 175.3, 173.8, 170.5, 133.1, 132.9, 132.4, 132.3, 100.9 (S-2), 99.4 and 99.3 (F-1), 75.6 (2 lines, F-4); 73.1, 72.8, 72.0, 70.9, 70.6, 69.4, 69.3, 68.5, 68.4, 67.9, 67.4, 64.6, 63.3, 62.8, 55.2, 52.2, 49.1(S-5), 40.7(S-3), 40.5 and 39.5 (L-1), 28.6 and 28.1 (both 2 lines, L-5 and L-6), 22.3 (NHAc), 13.1 and 12.8 (F-6).

m/z

Example 16

16.1: α-O-Methyl-2,3-di-O-benzoyl-4S-(prop-2'-en-1'-yl)-L-fucopyranoside (E23)

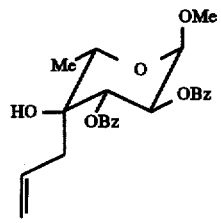

Allyl silane (4.45 g, 39 mmol) was added to a stirred solution of E1 (10.0 g, 26 mmol) and titanium tetrachloride (39 ml of a 1M solution in dichloromethane, 39 mmol) in dichloromethane (120 ml) at –78° C. under argon. The reaction mixture was held at –78° C. until it solidified (20 min), then at –20° C. for 3 hr, and then poured into NaHCO$_3$ (aq).(200 ml) and stirred until the aqueous layer became colourless. The organic layer was separated, washed with brine (100 ml), dried over magnesium sulphate and evaporated under reduced pressure to give pure axial homoallylic alcohol E23 as a clear oil (9.0 g, 21 mmol, 81% yield).

$^1$H nmr δ (CDCl$_3$) 8.0 (4H, 2xd, OBz); 7.5 (2H, 2xt, OBz); 7.4 (4H, 2xOBz); 6.08 (H, m, —CH=); 5.22 (H, d, F-3); 5.43 (H, dd, F-2); 5.29 and 5.15 (2H, m, CH$_2$=); 5.13 (H, d, F-1); 4.11 (H, q, F-5); 3.41 (3H, s, F-OMe); 3.18 (H, br s, OH); 2.8–2.56 (2H, 2xdd, —CH$_2$—); 1.38 (3H, d, F-OMe).

NOE experiment (CDCl$_3$): Irradiation of the allylic CH$_2$ resulted in an 11% enhancement at F-2, 6% at F-6 and 5% at the olefinic CH$_2$ signals. This is only consistent with an axial allylic substituent.

$^{13}$C nmr (CDCl$_3$) δ 167.3 (OCOPh), 166.0 (OCOPh), 133.8 (—CH=), 133.4, 133.2, 129.9, 129.8, 129.2, 128.4, 128.3, 118.4 (CH$_2$=), 96.8 (F-1), 74.9 (F-4), 70.7, 70.0, 55.2 (F-OMe), 34.4 (allyl CH$_2$), 14.0 (F-6).

16.2: α-O-Methyl-2,3-di-O-benzoyl-4S-(2'(S and R) ,3'-epoxypropan-1'-yl)-L-fucopyranoside (E24)

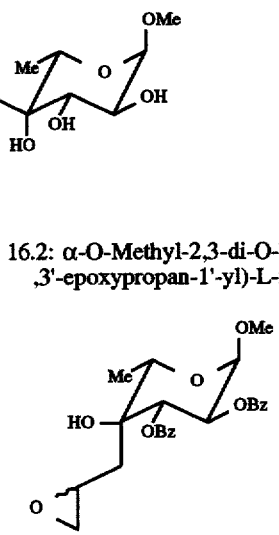

Excess technical grade (80% pure) metachloroperbenzoic acid (15g, 70 mmol) was added in 3 portions over 5 hr to a refluxing solution of E23 (9.21 g, 21.6 mmol) in dichloromethane (200 ml) at 50° C. The reaction mixture was cooled, stirred for 30 min with a saturated solution of sodium thiosulphate and sodium carbonate (200 ml), separated, and the organic layer was washed with brine and dried over MgSO$_4$. Evaporation gave a 1:1 mixture of the desired epoxides E2a as an oil (8.77 g, 19.9 mmol, 92% yield).

$^1$H nmr (CDCl$_3$) δ 8.01–7.92 (4H, m, OBz); 7.51–7.27 (6H, m, OBz); 5.78 and 5.74 (H, 2xd, J=10.6 and 10.6 Hz, F-3); 5.36 (H, dd, J=3.9 and 10.6 Hz, F-2); 5.10 and 5.07 (H, 2xd, J=3.9 Hz, F-1); 4.09 (H, m, F-5); 3.66–3.55 (H, br m); 3.41 and 3.40 (3H, 2xs, F-OMe); 3.37–3.28 (H, m, H-2'); 2.78 (H, m, H-3a'); 2.59 (H, m, H-3b'); 2.22–1.90 (2H, m, —CH$_2$—); 1.33 (3H, d, J=6.6 Hz).

$^{13}$C nmr δ (CDCl$_3$) 165.9 (several lines), 134.5–128.3 (several lines OBz), 96.9, 77.0, 76.7, 75.5, 75.4, 70.5, 70.1, 70.0, 55.3, 49.2, 48.8, 47.8, 33.2, 32.7, 13.7, 13.5.

m/z 16.3: α-O-Methyl-2,3-di-O-benzoyl-4S-(3'bromo-2'[S and R]-hydroxypropan-1'-yl)-L-fucopyranoside (E25)

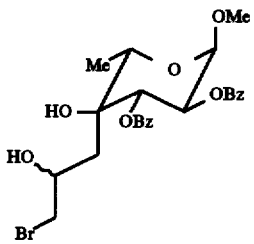

Nickel dibromide (6.97 g, 32 mmol) and lithium bromide (5.57, 64 mmol) were heated under reflux for 3 hr at 80° C. in anhydrous tetrahydrofuran (100 ml) to afford a deep blue solution of Li$_2$NiBr$_4$ (32 mmol). E24 (8.8 g, 20 mmol) was added to this solution and heated under reflux at 80° C. for 3 hr and then evaporated. The residue was taken up in ethyl acetate (200 ml) and citric acid (100 ml). The organic phase was separated, washed with brine, dried over MgSO$_4$ and evaporated to give the bromohydrins E25 as a white foam (10.24 g, 19.6 mmol, 98% yield).

$^1$H nmr (CDCl$_3$) δ 8.1–7.9 (4H, m, OBz); 7.47–7.27 (6H, m, OBz); 5.9 and 5.75 (H, 2×d, F-3); 5.35 and 5.15 (H, 2×dd, F-2); 5.08 (H, dd, F-1); 4.6 and 4.26 (2H, m, F-5 and H); 4.03 (H, m, CHOH); 3.45 (2H, m, CH$_2$Br); 3.40 (3H, s, F-OMe); 2.3–1.99 (2H, m, —CH$_2$—); 1.35 (3H, 2×d, F-6).

$^{13}$C nmr (CDCl$_3$) δ 167.9, 166.8, 166.6, 166.0, 134.4, 133.1, 130.0, 129.8, 129.6, 129.3, 129.8, 128.4, 128.3, 128.1, 97.7, 77.7, 77.1, 76.6, 76.6, 75.9, 75.4, 75.1, 71.2, 71.0, 70.1, 69.8, 69.2, 67.9, 55.2, 53.4, 39.0, 38.3, 32.8, 32.2, 25.5, 13.9, 13.3.

16.4: α-O-Methyl-2,3-di-O-benzoyl-4S-(3'bromo-2'-oxo-prop-1'-yl)-L-fucopyranoside (E26)

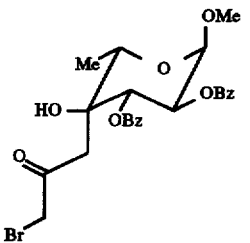

E25 (0.5 g, 9.6×10$^{-4}$M) was stirred with two equivalents of pyridinium chlorochromate (412 mg, 1.91×10-3M) and powdered 4A sieves (0.5 g) in anhydrous dichloromethane (10 ml) for 15 hr under argon. The reaction mixture was concentrated, resuspended in ether and passed through a 5 cm of pad of silica. The pad was flushed with additional portions of ether until no more compound was observed by tlc of the eluted fractions. Evaporation in vacuo gave the ketone E26 in about 90% purity as white foam. (0.39 g, 7.5×10$^{-4}$M, 78% yield)

$^1$H nmr (CDCl$_3$) δ 7.95–7.85 (4H, m, OBz); 7.53–7.27 (6H, m, OBz); 5.84 (H, d, J=10.8 Hz, F-3); 5.24 (H, dd, J=4.0 and 10.8 Hz, F-2); 5.09 (H, d, J=4.0 Hz, F-1); 4.86 (H, s, OH); 4.10 (H, q, J=6.3 Hz, F-5); 4.06 (2H, s, BrCH$_2$—); 3.41 (3H, s, F-OMe) 3.30 (H, d, J=17.3 Hz, CO—C HaHb-COH); 2.97 (H, d, J=17.3 Hz, CO—CHaHb-COH); 1.27 (3H, d, J=6.3 Hz, F-6).

$^{13}$C nmr (CDCl$_3$) δ 203.4, 166.2, 166.0, 133.4, 129.8 (4 lines), 129.3, 129.1, 128.5 (4 lines), 96.8, 76.4, 75.5, 69.3, 68.7, 55.3, 36.6, 35.7, 13.9.

m/z 16.5: α-O-Methyl-2,3-di-O-benzoyl-4S-(3'-diisopropoxyphosphono-2'-oxo-prop-1'-yl)-L-fucopyranoside (E27)

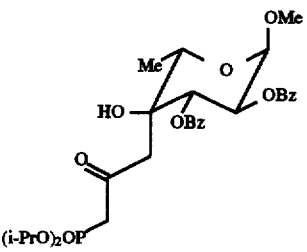

Impure ketone E26 (1.28 g, 2.5 mmol) was heated at 80° C. in triisopropyl phosphite (10 ml) for 4 hr. The solvent was removed by kugelrohr distillation at 125° C. and 1 mm Hg pressure to give a yellow oil. Flash chromatography using gradient elution; 20% ethyl acetate hexane rising to neat ethyl acetate gave three products:

α-O-Methyl-2,3-di-O-benzoyl-4S-(2'-oxoprop-1'-yl)-L-fucopyranoside (0.10 g, 2.3×10$^{-4}$M, 9% yield) Rf (ethyl acetate) 0.70

$^1$H nmr (CDCl$_3$) δ 7.9–7.85 (4H, m, OBz); 7.5–7.27 (6H, m, OBz); 5.87 (H, d, F-3); 5.17 (H, dd, F-2); 5.08 (H, d, F-1); 4.09 (H, q, F-5); 4.43 (3H, s, F-OMe); 3.07 (H, d, CO—C HaHb-COH); 2.88 (H, d, CO—CHaHb-COH); 2.36 (3H, s, CH$_3$—CO—); 1.26 (3H, d, F-6).

α-O-Methyl-2,3-di-O-benzoyl-4S-(2'-diisopropoxyphosphate-prop-3'-en-1'-yl)-L-fucopyranoside (0.28 g, 4.3×10-4M, 18% yield) Rf (ethyl acetate) 0.57

$^1$H nmr (CDCl$_3$) δ 7.93 (2H, d, J=7.1 Hz, OBz); 7.63 (2H, d, J=7.3 Hz, OBz); 7.42–7.19 (6H, m, OBz); 5.78 (H, d, J=10.9 Hz, F-3); 5.21 (H, dd, J=4.0 and 10.9 Hz, F-2); 5.05 (H, d, J=4.0 Hz, F-1); 4.96 and 4.79 (2H, 2×s, =CH$_2$); 4.6–4.38 (4H, m, P(—O—CH)$_2$); 4.3 (H, br s, OH); 4.02 (H, q, F-5); 3.31 (3H, s, F-OMe); 2.86 (H, d, J=15.2 Hz, CO—C HaHb-COH); 2.76 (H, d, J=15.2 Hz, CO—CHaHb-COH); 1.25 (6H, d, J=6.3 Hz, 2×isopropyl CH$_3$); 1.17 (6H, d, J=6.3 Hz, 2×isopropyl CH$_3$); 1.02 (3H, d, J=6.2 Hz, F-6).

$^{13}$C nmr (CDCl$_3$) δ 166.6 (OCOPh), 165.9 (OCOPh), 152.6 (J$_{CF}$=32.3 Hz, =C—O—P), 133.1, 132.0, 129.8, 129.7, 129.6, 129.1, 128.2, 128.1, 102.1 (J$_{CF}$=19.8 Hz, H$_2$ C=C—O—P), 96.7 (F-1), 75.6 (F-4), 75.1, 73.4 (3 lines J$_{CF}$=24.8 and 29.0 Hz, 2×isopropyl O—CH), 70.9, 70.2, 55.1 (F-OMe), 34.1 (J$_{CF}$=13.5 Hz, P—O—C—CH$_2$—COH), 23.5–23.1 (6 lines, 4×isopropyl CH$_3$), 13.3 (F-6).

m/z
and

α-O-Methyl-2,3-di-O-benzoyl-4S-(3'-diisopropoxyphosphono-2'-oxo-prop-1'-yl)-L-fucopyranoside (E27): A white foam (0.490 g, 35% yield) Rf (ethyl acetate) 0.45

$^1$H nmr (CDCl$_3$) δ 7.93–7.85 (4H, m, 2×OBz); 7.5–7.25 (6H, m, 2×OBz); 5.87 (H, d, F-3); 5.35 (H, br s, OH); 5.17 (H, dd, F-2); 5.09 (H, d, F-1); 4.75–4.55 (2H, m, 2×isopropyl CHs); 4.06 (H, q, F-5); 3.39 (3H, s, F-OMe); 3.30–2.95 (4H, m, P—CH$_2$—COCH$_2$—); 1.30 (15H, 3×d, F-6 and 4×isopropyl CH$_3$s).

$^{13}$C nmr (CDCl$_3$) δ 203.2 (J$_{CF}$=Hz, ketone CO), 165.8, 165.7, 133.1, 129.8, 129.7, 129.6, 129.4, 129.0, 128.3, 96.6 (F-1), 76.2 (F-4); 75.6, 75.0, 74.6, 73.4, 71.8 (J$_{CF}$=Hz), 70.2, 69.6, 55.1, 46.6, 44.6, 40.9, 23.8, 13.8.

m/z 16.6: α-O-Methyl-2,3-di-O-benzoyl-4S-[{tetra-O-acetyl-N-acetyl-α2"-neuraminidyl methyl ester}5'-oxy-2'-oxo-pent-3'-en-1'-yl]-L-fucopyranoside (E28)

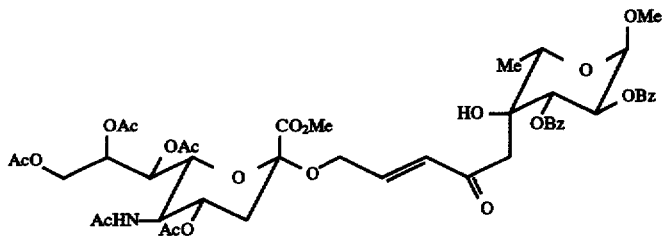

A suspension of caesium carbonate (180 mg, 5.5×10$^{-4}$M), E4 (300 mg, 5.37×10$^{-4}$M) and E27 (300 mg, 4.95×10$^{-4}$M) were stirred in t-butanol (7 ml) at between 25° C. and 30° C. to give an intense yellow solution. The reaction was quenched after 100 minutes with 2M HCl (aq) (0.5 ml) and azeotroped to dryness with toluene. The residue was flash chromatographed on silica (45 g) using 80% ethyl acetate-hexane to give first recovered E27, then secondly enone E28 as a white foam (180 mg, 1.9×10$^{-4}$M, 38% yield.

$^1$H nmr (CDCl$_3$) δ 7.94 (2H, d, J=8.1 Hz, OBz); 7.88 (2H, d, J=8.0 Hz, OBz); 7.48 (2H, t, J=7.3 Hz, OBz); 7.37–7.27 (2H, m, OBz); 6.89 (H, dt, J=3.6 and 15.8 Hz, L-4); 6.48 (H, d, J=15.8 Hz); 6.01 (H, s); 5.87 (H, d, J=10.6 Hz, F-3); 5.41–5.31 (2H, m); 5.15 (H, dd, J=10.6 and 4.0 Hz, F-2); 5.14 (H, m); 5.09 (H, d, J=4.0 Hz, F-1); 4.92 (H, m, S-4); 4.55 (H, br d, J=16.9 Hz); 4.29 (H, dd, J=2.2 and 12.5 Hz); 4.16–4.03 (5H, m, F-5, 1×S-9, 1×L-5, S-6, S-5); 3.78 (3H, s, S-OMe); 3.40 (3H, s, F-OMe); 3.12 and 3.02 (2H, 2×d, J=16.8 Hz, L-1); 2.68 (H, dd, J=4.6 and 12.9 Hz, S-3e); 2.16, 2.13, 2×2.04 (12H, 4×s, 4×OAc); 2.10 (H, dd, S-3a); 1.90 (3H, s, NHAc); 1.22 (3H, d, J=7.0 Hz, F-6).

$^{13}$C nmr (CDCl$_3$) δ 202.0 (L-2, ketone), 171.1, 170.8, 170.6, 170.2, 170.0, 168.0, 166.0, 165.6, 143.7, 133.2, 132.9, 129.8, 129.7, 129.6, 129.3, 129.1, 128.3, 128.2, 98.4 (S-2), 96.7 (F-1), 76.9, 74.8, 72.6, 71.0, 69.4, 68.9, 68.2, 67.2, 63.4, 62.4, 60.4, 55.2 (F-OMe), 52.8 (S-OMe), 49.3 (S-5), 37.9 (S-3), 35.6 (L-1), 23.1 (NHAc), 21.1, 20.9, 20.8, 20.7, 14.1 (F-6).

m/z

Example 17

O-Methyl-2,3-di-O-benzoyl-4S-[{tetra-O-acetyl-N-acetyl-α2"-O-neuraminidyl methyl ester}5'-oxy-2'(R and S)-hydroxy-pent-3'-en-1'-yl]-L-fucopyranoside (E29)

and

O-Methyl-2-O-benzoyl-4S-[{tetra-O-acetyl-N-acetyl-α2"-neuraminidyl methyl ester}5'-oxy-2'(R and S)-hydroxy-pent-3'-en-1'-yl]-L-fucopyranoside (E30)

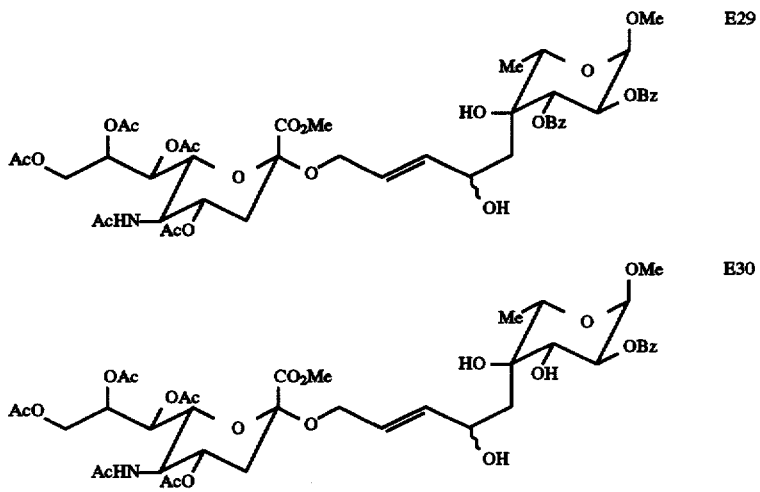

E28 (150 mg, 1.56×10$^{-4}$M) was converted into E29 using NaBH$_4$ (12 mg, 3.1×10$^{-4}$M) and CeCl$_3$7H$_2$O (117 mg, 3.1×10$^{-4}$M) in methanol (10 ml) according to the method described for E9. After chromatography on silica (eluant ethyl acetate), E29 (49 mg, 5.1×10$^{-5}$M)(2 epimers) and E30 (36 mg, 4.2×10$^{-4}$M)(1 epimer) were obtained as a yellow oils.

E29 spectral data:

¹H nmr (CDCl₃) δ 8.0–7.9 (4H, m, OBz); 7.5–7.25 (6H, m, OBz); 5.9–5.75 (2H, 2×d and m, F-3 of both epimers and H); 5.45–5.15 (4H, m, F-2, 3H); 5.09 (H, d, F-1); 4.87 (H, m); 4.37–3.9 (8H, m); 3.80 (4H, s+m, S-OMe+H); 3.40 (3H, s, F-OMe), 2.63 (H, dd, S-3e); 2.18 (6H, 2×s, 2×OAc); 2.05 (6H, 2×s, 2×OAc); 2.1–1.65 (3H, m); 1.28 (3H, 2×d, F-6).

E30 spectral data:

¹H nmr (CDC₃) δ 8.09 (2H, d, OBz); 7.56 (H, t, OBz); 7.46 (2H, t, OBz); 5.82 (2H, m); 4.97 (H, dr); 5.29 (2H, d +m): 5.05 (H, dd, F-2); 4.96 (H, d, F-1); 4.87 (H, m); 4.58 (H, dd); 4.35 (H, dd); 4.25 (H, dd); 4.18 (7H, m); 3.8 (3H, s, S-OMe); 3.38 (3H, s, F-OMe); 2.62 (H, dd, S-3e); 2.18 and 2.17 (6H, 2×s, 2×OAc); 2.05 (6H, 2×OAc); 1.70 (2H, m, L-1); 1.28 (3H, 2×d, F-6).

¹³C nmr (CDCl₃) δ 171.1, 171,1, 170.3, 168.5, 166.4, 135.1, 133.1, 129.9, 128.3, 126.4, 98.7 (S-2), 97.2 (F-1), 75.1, 74.7, 72.7, 72.6, 70.1, 69.0, 68.7, 68.4, 67.5, 65.0, 62.9, 55.2 (F-OMe), 52.8 (S-OMe), 49.3 (S-5), 37.9 (S-3), 34.9 (L-1), 23.1 (NHAc), 21.1 and 20.8 [3 lines](4×OAc), 13.7 (F-6).

Only one of the two possible epimers of E30 has been isolated.

Example 18

α-O-Methyl-4S-[{N-acetyl-α2"-neuraminidyl carboxylic acid}5'-oxy-2'(R and S)-hydroxy-pent-3'-en-1'-yl]-L-fucopyranoside (E31)

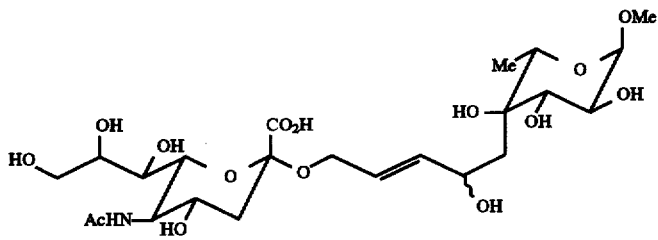

E29 (49 mg, 5.1×10⁻⁵M) and E30 (36 mg, 4.2×10⁻⁴M) were stirred with 5 equivalents of sodium methoxide (24 mg, 4.5×10⁻⁴M) in methanol (5 ml) at room temperature for 20 hr. The reaction mixture was neutralised using Dowex H⁺ resin and evaporated under reduced pressure. The residue was flash chromatographed on silica eluant 10% rising to 30% methanol-chloroform to give a fraction containing the disaccharide as an oil (29 mg). Partial hydrolysis of the sialic acid methyl ester had occurred, therefore the material was redissolved in 0.1M sodium deuteroxide in D₂O (0.5 ml) to complete the conversion to the sodium carboxylate salt (24 hr). The solution was made acidic with Dowex H⁺ resin and the solvent was removed to give the carboxylic acids E31 as a clear viscous oil (19 mg, 3.3×10⁻⁵M).

¹H nmr (D₂O) δ 5.9–5.9 (2H, m, L-3, L-4); 4.7 (H, d, F-1); 4.1–3.5 (16H, m); 3.38 (3H, s, F-OMe); 2.68 (H, dd, S-3e); 2.4 (H, dd, S-3a); 2.0 (3H, s, NHAc); 1.95–1.6 (2H, m, L-1); 1.22 (3H, d, F-6).

¹³C nmr (D₂O) δ 175.2, 171.6, 134.9, 126.3, 99.2, 77.5, 71.1, 70.6, 70.3, 68.9, 68.4, 67.6, 67.0, 66.9, 64.8, 63.4, 63.2, 55.4, 52.3, 52.0, 39.6, 38.9, 22.3, 14.2.

Example 19

The following examples describe the syntheses of starting materials useful in the preparation of compounds of the invention by methods analagous to those of examples 1, 12 and 16 above.

19.1: α-O-Methyl-2,3-di-O-benzoyl-4S-(2'oxoethyl)-L-fucopyranoside (E32)

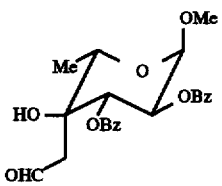

E23 (0.52 g, 1.22 mmol) was ozonolysed in dichloromethane (50 ml) at 0° C. until after 2 hr no starting material remained. Dimethyl sulphide (2 ml) was added and the reaction mixture was left to stand overnight. Evaporation of the solvent in vacuo gave the aldehyde as an oil (0.41 g, 9.58×10⁻⁴M).

¹H nmr (CDCl₃) δ 9.8 (H, s, CHO); 8.17–7.9 (4H, m, OBz); 7.6–7.2 (6H, m, OBz); 5.75 (H, d, F-3); 5.25 (H, dd, F-2); 5.16 (H, d, F-1); 4.17 (H, q, F-5); 4.42 (3H, s, F-OMe); 3.0 (H, dd, OHC—C*H*aHb-); 2.85 (H, dd, OHC—CHa H*b*-); 1.38 (3H, s, F-6).

m/z 19.2: α-O-Methyl-2,3-di-O-benzoyl-4S-(carboxymethylene)-L-fucopyranoside (E33)

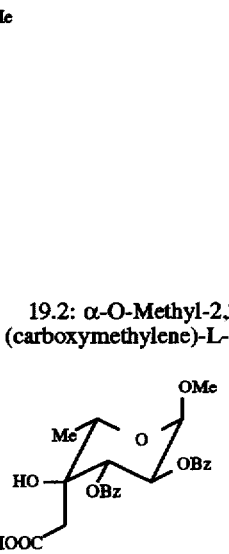

E23 (0.52 g, 1.22 mmol) was stirred with hydrated ruthenium trichloride (15 mg) and sodium periodate (1.0 g.) in a (3:2:2) mixture of water, acetonitrile and carbon tetrachloride (18 ml) for 2 hr at room temperature. The mixture was extracted with dichloromethane (2×50 ml), evaporated to dryness, resuspended in ether (100 ml), and filtered through celite. The ethereal solution was concentrated to 20 ml and extracted twice with saturated sodium bicarbonate (2×25 ml). The aqueous layer was acidified with concentrated HCl and extracted with dichloromethane (2×25 ml). Drying over MgSO₄ and removal of the solvent in vacuo gave acid E33 as a white foam (0.29 g, 6.5×10⁻⁴M, 53% yield).

¹H nmr (CDCl₃) δ 7.97–7.87 (4H, m, OBz); 7.47 (6H, m, OBz); 5.86 (H, d, F-3); 5.20 (H, dd, F-2); 5.10 (H, d, F-1);

4.13 (H, q, F-5); 3.40 (3H, s, F-OMe); 2.89 (H, d, HOOC—CHaHb); 2.70 (H, d, HOOC—CHaHb); 1.29 (3H, d, F-6)

19.3: α-O-Methyl-2,3-di-O-benzoyl-4S-(methylcarboxymethylene)-L-fucopyranoside (E34)

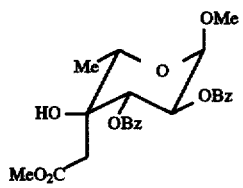

Diazomethane (derived from 1 g of Diazaid according to the method of P. Lombardi, Chemistry and Industry, 1990, 21, 708) was blown through an ice cold solution of E33 (0.290 g, 6.5×10$^{-4}$M) in dichloromethane (30 ml)-methanol (10 ml). After 45 min no starting material remained in the yellow solution. Argon was blown through the solution for 5 min and the solvent was removed to give pure ester E34 (0.302 g, 100% yield).

$^1$H nmr (CDCl$_3$) δ 7.97–7.87 (4H, m, OBz); 7.47 (6H, m, OBz); 5.86 (H, d, F-3); 5.17 (H, dd, F-2); 5.10 (H, d, F-1); 4.13 (H, q, F-5); 3.58 (3H, s, CO$_2$Me); 3.37 (3H, s, F-OMe); 2.91 (H, d, MeOOC—CHaHb); 2.75 (H, d, MeOOC—CHaHb); 1.29 (3H, d, F-6).

$^{13}$C nmr (CDCl$_3$) δ 174.0, 166.0, 133.2 133.1, 129.8, 129.7, 128.3 (2 lines), 96.6, 75.3, 74.8, 68.8, 55.2, 52.2, 31.4, 13.6.

19.4: 4-Oxo-1,2,3-tri-O-benzoyl fucose α pyranoside (E35)

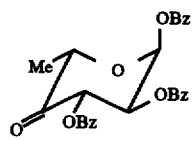

1,2,3-tri-O-benzoyl fucose α pyranoside (5.6 g, 15 mmol) prepared by the method of Theim et al, Carbohydrate Research 1991, 209,119 was stirred with excess PCC (14.6 g, 68 mmol) and powdered 4A molecular sieves (30 g) in dichloromethane (150 ml) for 24 hr. The reaction mixture was columned on fluorosil to give the ketone as a white foam. (3.6 g, 9.4 mmol) 78% yield.

$^1$H nmr (CDCl$_3$) δ 8.18–7.27(15H, m); 6.93 (H, d, J=3.7 Hz, F-1); 6.27 (H, d, J=10.9 Hz, F-3); 5.92 (H, dd, J=3.7 and 10.9 Hz); 4.75 (H, q, J=6.5 Hz, F-5); 1.45 (H, d, J=6.5 Hz, F-6).

$^{13}$C nmr (CDCl$_3$) δ 195.2, 164.2, 163.6, 163.0, 132.7, 132.3, 128.7, 128.4, 127.4, 127.1, 88.6, 73.1, 70.6, 69.9, 12.6.

m/z

19.5: 6-Deoxy-4S-[prop-2'-en-1'-yl]-1,2,3-tri-O-benzoyl-L-glucose α pyranoside (E36)

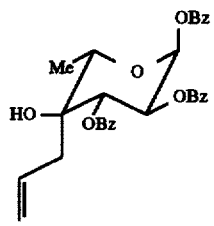

Titanium tetrachloride (4 ml, 20 mmol) was added dropwise to a stirred solution of E34 (2.50 g, 6.7 mmol) and allyl trimethylsilane (1.53 g, 13.4 mmol) in anhydrous dichloromethane (80 ml) under argon at −78° C. The reaction mixture was stirred at −78° C. for 30 min then at −20° C. for 30 min and quenched with 2M HCl (aq) (100 ml). The organic layer was washed once with ammonium acetate solution (ml), dried and evaporated to give the axial homoallylic alcohol E35 as a white foam (2.46 g, 5.9 mmol) 88% yield.

$^1$H nmr (CDCl$_3$) δ 8.18–7.26 (15H, m); 6.73 (H, d, J=3.9 Hz, F-1); 6.09 (H, m, —CH=); 5.87 (H, d, J=10.8 Hz, F-3); 5.76 (H, dd, J=3.9 and 10.8 Hz); 5.31–5.17 (2H, m, CH$_2$=); 4.35 (H, q, J=6.6 Hz, F-5); 3.22 (H, br s, OH); 2.81 (H, dd, J=7.1 and 14.6 Hz, —CH$_a$H$_b$-); 2.68 (H, dd, J=7.1 and 14.6 Hz); 1.45 (H, d, J=6.5 Hz, F-6).

$^{13}$C nmr (CDCl$_3$) δ 165.9, 164.1, 163.2, 132.2–126.9 (10 lines), 117.9, 88.7, 75.6, 73.2, 72.0, 67.5, 33.0, 12.7.

m/z

19.6: 6-Deoxy-4S-(2'-oxoethyl)-1,2,3-tri-O-benzoyl-L-glucose α pyranoside (E37)

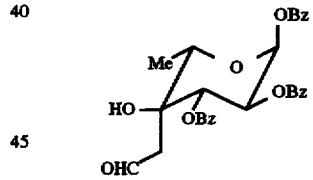

A solution of E36 (1.0 g, 2.4 mmol) in dichloromethane (20 ml) was ozonolysed at 0° C. until after 40 min no starting material remained. Dimethyl sulphide (1 ml) and methanol (2 ml) were added and the reaction mixture was left overnight. The solution was washed with water (50 ml), dried and evaporated to give crude aldehyde E36 as a white foam (0.82 g, 1.96 mmol) 82% yield. The purity was estimated to be 90% by $^1$H nmr.

$^1$H nmr (CDCl$_3$) δ 10.01 (H, t, J=1.6 Hz, CHO); 8.13–7.26 (15H, m, 3×OBz); 6.73 (H, d, J=4.1 Hz, F-1); 5.96 (H, d, J=9.8 Hz, F-3); 5.57 (H, dd, J=4.1 and 9.8 Hz); 4.35 (2H, q, J=6.4 Hz, F-5, OH); 3.07 (H, dd, J=1.6 and 16.5 Hz, —CHaHb-); 2.88 (H, dd, J=1.6 and 16.5 Hz, —CHaHb-); 1.31 (H, d, J=6.4 Hz, F-6)

$^{13}$C nmr (CDCl$_3$) δ 200.7, 165.9, 164.3, 162.9, 132.4–127.0 (7 lines), 88.4, 74.3, 71.4, 67.6, 40.0, 12.8.

m/z

19.7 6-Deoxy-4S-(t-butylcarboxy-3'-prop-2'[Z and E]-en-1'-yl)-1,2,3-tri-O-benzoyl-L-glucose α pyranoside (E38 and E39)

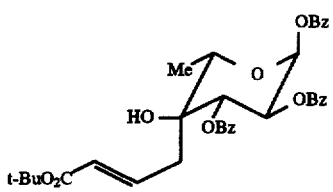  E39

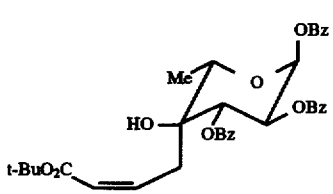  E38

Crude aldehyde E37 (0.3 g, 7.2×10⁻⁴M) was stirred with t-butylcarboxymethylenetriphenylphosphorane (3.2 g, 8.6×10⁻⁴M) in dichloromethane (15 ml) for 17 hr at room temperature. The reaction mixture was evaporated and the residue flash columned on silica; eluant 3% ethanol-dichloromethane, to afford the cis isomer E36 (oil, 36 mg, 7.0×10⁻⁵M, 10% yield, Rf 0.66 in 5% ethanol-dichloromethane) and the trans isomer E37 (yellow oil, 289 mg, 5.6×10⁻⁴M, 78% yield, Rf 0.60 in 5% ethanol-dichloromethane).

E38 Z-isomer:

¹H nmr (CDCl₃) δ 8.15–7.22 (15H, m, 3×OBz); 6.74 (H, d, J=4.0 Hz, F-1); 6.59 (H, m, J=9.1 and 11.4 Hz, H-3'); 6.02 (H, d, J=11 Hz, F-3); 5.86 (H, d, J=11.4 Hz); 5.65 (H, dd, J=4.0 and 10.9 Hz, F-2); 5.21 (H, br s, OH); 4.36 (H, q, J=6.4 Hz, F-5); 3.15 (2H, d, CH₂); 1.42 (9H, s, t-Bu); 1.34 (3H, d, J=6.4 Hz, F-6).

E39, E-isomer:

¹H nmr (CDCl₃) δ 8.12–7.25 (16H, m, 3×OBz, F-1); 7.08 (H, dt, J=7.4 and 15.6 Hz, H-2'); 5.90 (H, d, J=15.6 Hz, H-3'); 5.75 (H, d, J=10.7 Hz, F-3); 5.68 (H, dd, J=3.8 and 10.7 Hz, F-2); 4.33 (H, q, J=6.5 Hz, F-5); 3.60 (H, br s, OH); 2.85 (H, dd, J=9.1 and 16.3 Hz, —CHaHb-); 2.72 (H, dd, J=9.1 and 16.3 Hz, —CHaCHb-); 1.35 (9H, s, t-Bu); 1.34 (3H, d, J=6.5 Hz, F-6).

¹³C nmr (CDCl₃) δ 164, 163.8, 163.5, 163.2, 140.9, 132.4–126.9 (9 lines), 124.2, 88.5, 78.7, 75.6, 73.8, 72.1, 67.4, 31.0, 26.6, 12.5.

19.8: 6-Deoxy-4S-(t-butylcarboxy-3'-prop-2'E-en-1'-yl)-4-O-acetyl-1,2,3-tri-O-benzoyl-L-glucose α pyranoside (E40)

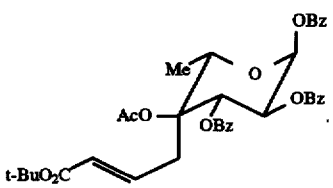

E39 (0.77 g, 1.4 mmol) was stirred with 5 equivalents of acetic anhydride (1 ml) and methylamine (1.5 ml) and a catalytic amount of DMAP in dichloromethane (20 ml) for 18 hr at room temperature. The solution was washed with 2M HCl (aq), dried and evaporated to give an oil. Flash chromatography on silica eluant 20% ethyl acetate-hexane gave the product E40 as a clear oil (0.38 g, 0.57 mmol).

¹H nmr (CDCl₃) δ 8.21–7.17 (15H, m, 3×OBz); 7.12 (H, dt, J=7.2 and 15.6 Hz, H-2'); 6.92 (H, d, J=9.5 Hz, F-3); 6.74 (H, d, J=4.1 Hz, F-1); 5.98 (H, d, J=15.6 Hz, H-3'); 5.72 (H, q, J=6.5 Hz, F-5); 5.64 (H, dd, J=4.1 and 9.5 Hz, F-2); 3.10 (H, dd, J=6.9 and 15.7 Hz, —CHaHb-); 2.94 (H, dd, J=6.9 and 15.7 Hz, —CHaCHb-); 2.07 (3H, s, OAc); 1.43 (9H, s, t-Bu); 1.27 (3H, d, J=6.6 Hz, F-6).

¹³C nmr (CDCl₃) δ 168.6, 164, 164.0, 163, 140.9, 132.3–126.9, 123.6, 88.2, 82.2, 78.8, 69.2, 68.3, 66.2, 30.2, 26.7, 20.6, 12.6. 19.9: 6-Deoxy-4S-(carboxy-3'-prop-2'Z-en-1'-yl)-4-O-acetyl-1,2,3-tri-O-benzoyl-L-glucose αpyranoside (E41)

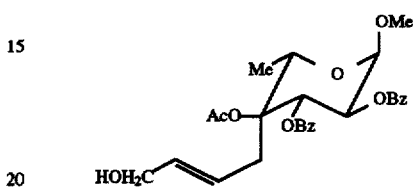

E40 (0.38 g, 5.7×10–4M) was stirred in a 3:7 mixture of trifluoroacetic acid and dichloromethane (10 ml) for 1 hr. The solvent was removed to give the carboxylic acid E38 as a clear oil (0.35 g, 5.7×10⁻⁴M) 100% yield.

¹H nmr (CDCl₃) δ 10.4 (H, br s, COOH); 8.21–7.21 (16H, m, 3×OBz, H3'); 6.95 (H, d, J=10.4 Hz, F-3); 6.78 (H, d, J=3.9 Hz, F-1); 6.13 (H, d, J=15.6 Hz, H-3'); 5.76 (H, q, J=6.5 Hz, F-5); 5.72 (H, dd, J=3.9 and 10.4 Hz, F-2); 3.19 (H, dd, J=7.8 and 16.4 Hz, —CHaHb-); 3.02 (H, dd, J=7.8 and 16.4 Hz, —CHaCHb-); 2.13 (3H, s, OAc); 1.31 (3H, d, J=6.6 Hz, F-6).

19.10: 6-Deoxy-4S(4'-hydroxy-but-2'Z-en-1'-yl)-1,2,3-tri-O-benzoyl-L-glucose α pyranoside (E42)

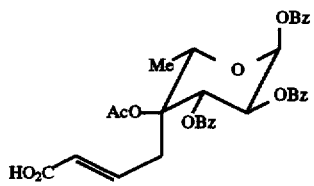

Ethyl chloroformate (93 mg, 8.6×10⁻⁴M) in tetrahydrofuran (1 ml) was added dropwise to a stirred solution of the acid E41 (0.35 mg, 5.7×10⁻⁴M) and triethylamine (87 mg, 8.6×10⁻⁴M) in tetrahydrofuran (3 ml) under argon at –5° C. The reaction mixture was stirred at this temperature for 45 min, then the triethylamine hydrochloride was filtered off and the filtrate added directly to a solution of sodium borohydride (65 mg, 1.72 mmol) in water (4 ml) at 10° C. The reaction mixture was stirred overnight at room temperature then quenched with 2M HCl (aq) (2 ml) and extracted with ether (2×20 ml). The organic layers were dried and evaporated to give an oil. Flash chromatography on silica eluant 50% ethyl acetate-hexane gave the product E39 as a clear oil (195 mg, 3.3×10–4M) 58% yield.

¹H nmr (CDCl₃) δ 8.26–7.18 (15H, m, 3×OBz); 6.93 (H, d, J=10.4 Hz, F-3); 6.70 (H, d, J=4.1 Hz, F-1); 6.01–5.93 (3H, m, F-2, —CH=CH—); 5.70 (H, q, J=6.6 Hz, F-5); 4.17 (2H, d, CH₂OH); 2.87 (2H, d, H₂-2'); 2.25 (H, br s, OH); 2.05 (3H, s, OAc); 1.31 (3H, d, J=6.6 Hz, F-6).

¹³C nmr (CDCl₃) δ 168, 164.3, 163, 132.3–126.9 (9 lines), 125.6, 88.4, 82.7, 69.5, 67.7, 66.3, 62.1, 31.7, 20.7, 12.6.

Biological Example

The test compounds were assayed to determine their effectiveness at inhibiting E-selectin mediated adhesion between a leucocytic cell line, U937, which expresses ligands for E-selectin, and a Chinese Hamster Ovary cell line which stably expresses E-selectin. The assay has been validated with a commercial known ligand of the E-selectin, 3'-sialyl-3-fucosyl lactose (3S'3FL).

In vitro assay protocol
Preparation of cells

A 96 well plate was seeded with E-selectin expressing CHO cells which were confluent on the day of the assay.

U937 cells were incubated overnight with $^3$H thymidine. (Incubation conditions: $2\times10^5$ U937 cells per ml, 0.0751 µCi $^3$H thymidine).

Preparation of reagents

Assay medium.

Hanks Balanced salts solution, 25 mM HEPES, 0.1% azide.

Test compounds.

Figure 3:
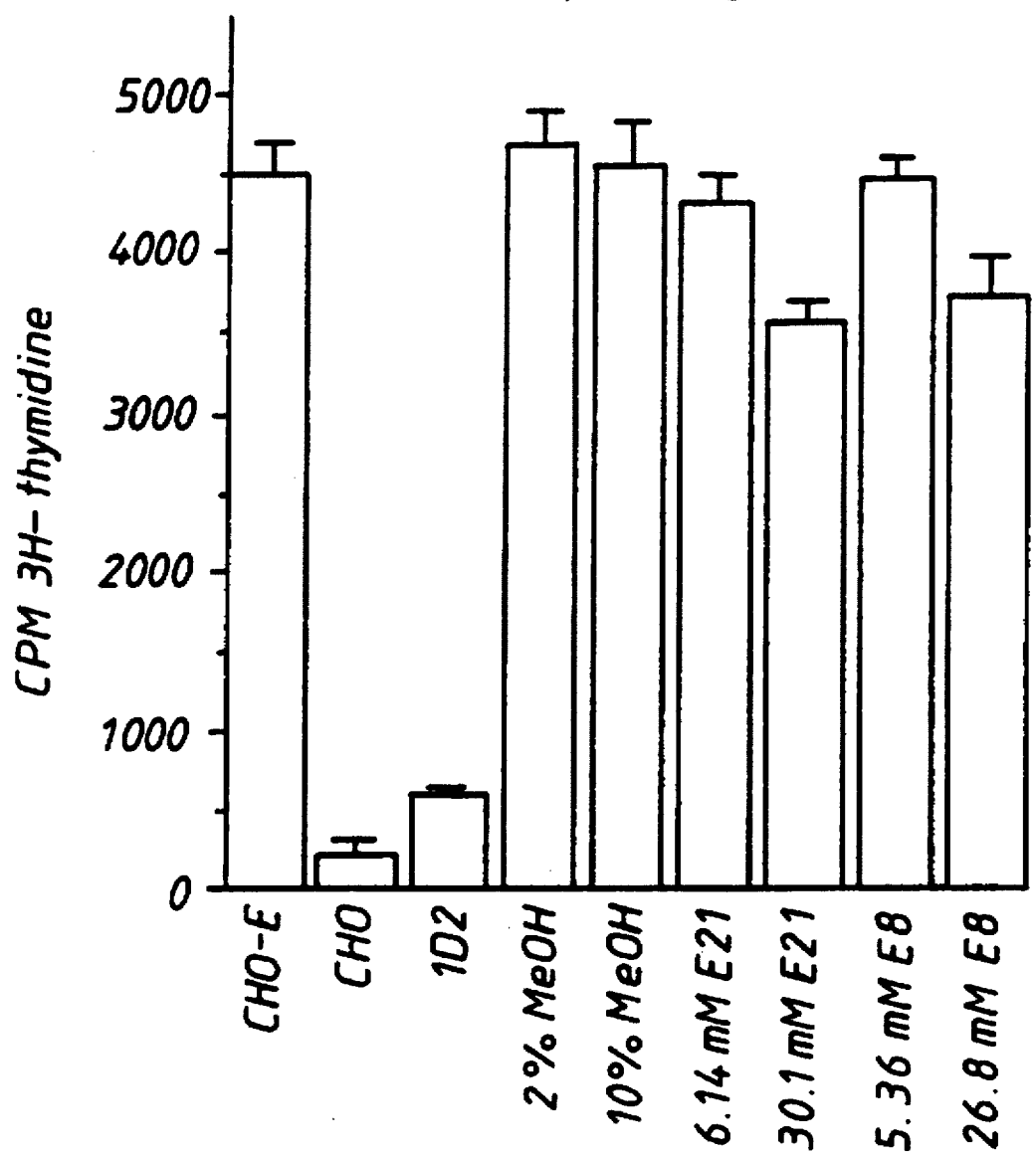

The compounds were dissolved in 1 ml of assay medium. For E8, 10% methanol was added to achieve a homogenous solution. In a control experiment, 10% percent methanol did not affect adhesion (FIG. 3).

The pH of the compounds was adjusted to approximately pH 7.2.

Controls

The $^3$H thymidine count value at each concentration of inhibitor is the average of six replicates. Maximum binding was measured by binding U937 cells to E-Selectin CHO cells in the absence of any test compounds.

Background was measured by U937 binding to untransfected CHO cells.

The adhesion between the U937 and E-selectin expressing CHO line was shown to be mediated by the E-selectin by blocking the interaction with an anti E-selectin antibody, 1D2 at 10 µg/ml.

Conditions of assay

On the day of assay the 96 well plate was washed 3 times in ice cold assay medium. 50 µl of test sample was added to each well and incubated on ice for 1 hour. Meanwhile the U937 cells were washed 3 times in ice cold assay medium, resuspended at a concentration of $3\times10^6$ cells per ml and then 50 µl was added to each plate. The plates were kept on ice and allowed to incubate at 4° C. for 1 hour. Then they were washed ×3 and the remaining cells solubilised and the radioactivity in the samples counted.

The U937 cells that were used in the 1D2 control were pre-incubated in the presence of 0.1 mg/ml gammaglobulin before addition to the plate.

Figure 2:
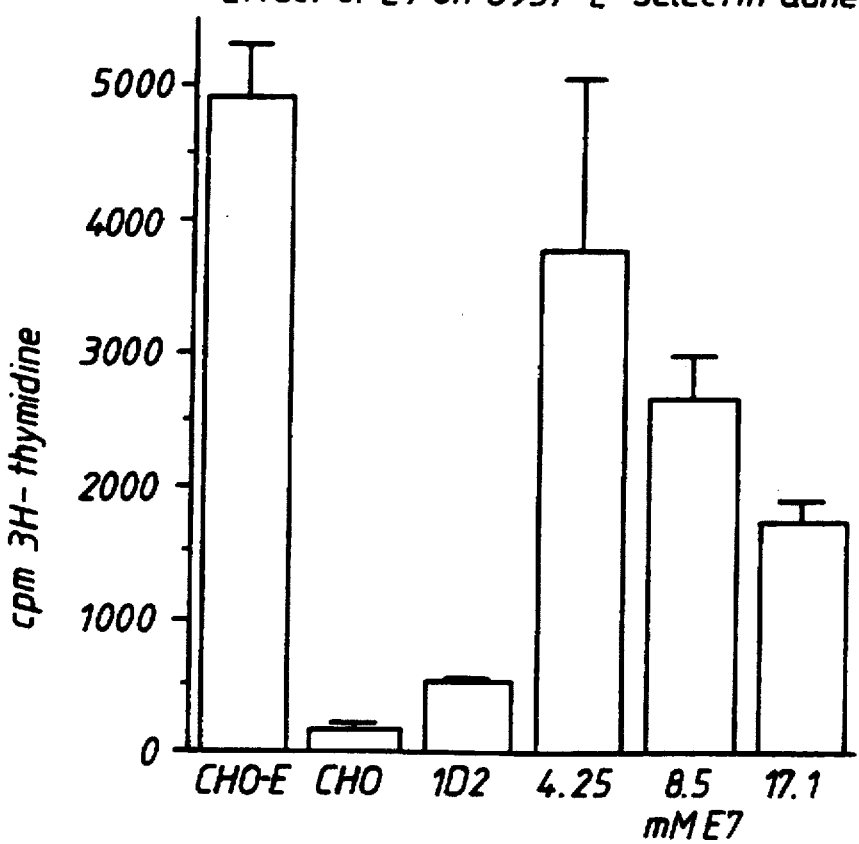

The results of three compounds E7, E8, E21 and the control, 3'S3FL are given (see FIGS. 1–3).

In FIG. 2:
Column 1; maximal binding of U937s to E-selectin expressing CHO cells.
Column 2; background adhesion of U937s to untransfected CHO cells.
Column 3; binding of U937s to E-selectin expressing CHO cells in the presence of 10 µg of 1D2 antibody.
Columns 4–6; binding of U937s to E-selectin expressing CHO cells in presence of 4.25, 8.5 and 17.1 mM of E7.

In FIG. 3:
Column 1; Maximum binding of U937s to E-selectin expressing CHO cells.
Column 2; Binding of U937s to untransfected CHO cells.
Column 3; Binding of U937s to E-selectin expressing CHO cells in the presence of 10 µg of 1D2 anti E-selectin antibody.
Column 4; Binding of U937s to E-selectin expressing CHO cells in assay medium containing 2% methanol.
Column 5; Binding of U937s to E-selectin expressing CHO cells in assay medium containing 10% methanol.
Columns 6 and 7; Binding of U937s to E-selectin expressing CHO cells in the presence of 6.14 and 30.1 mM of E21.
Columns 8 and 9; Binding of U937s to E-selectin expressing CHO cells in the presence of 5.36 and 26.8 mM of E8.

It is apparant that:
3'S3FL causes 54% inhibition of binding at 0.5 mM.
E7 causes 65% inhibition of binding at 17.1 mM.
E8 shows 18.5% inhibition of adhesion at 26.8 mM.
E21 shows 21% inhibition of adhesion at 30.7 mM.

We claim:

1. A compound of formula (I), or a salt, solvate or hydrate thereof:

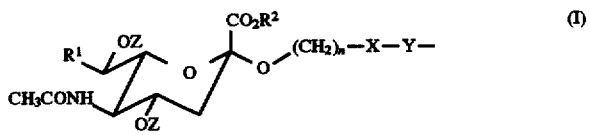

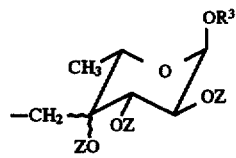

wherein:

X represents a divalent group selected from those of formulae I(a) to I(g) below

      I(a)

      I(b)

      I(c)

      I(d)

      I(e)

      I(f)

      I(g)

wherein $R_1$ and $R_2$ independently represent hydrogen, $C_{1-3}$ alkyl or —COOR$_6$ where $R_6$ is $C_{1-6}$ alkyl; and $R_3$ and $R_4$ independently represent hydrogen, hydroxyl or $C_{1-3}$ alkyl; and bonds a and b may be single or double;

Y represents a single bond or a divalent group selected from those of formulae I(h) to I(j) below

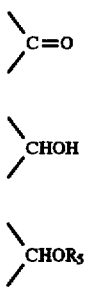

$\diagdown$C=O     I(h)

$\diagdown$CHOH     I(i)

$\diagdown$CHOR₅     I(j)

wherein

R₅ represents $C_{1-3}$ alkyl or a glycosyl residue;
each Z independently represents hydrogen or a hydroxyl protecting group;
$R^1$ represents hydrogen or a group —CH(OZ)CH₂(OZ) wherein Z has the meaning defined above;
$R^2$ represents hydrogen, a pharmaceutically acceptable cation, $C_{1-6}$ alkyl, $C_{2-6}$ alkenyl, or (optionally substituted)phenyl-($C_{1-4}$) alkyl;
$R^3$ represents hydrogen, $C_{1-6}$ alkyl, ($C_{1-4}$) alkyl-substituted phenyl or benzoate; and
n is 1, 2 or 3.

2. A compound as claimed in claim 1 wherein X is a group of formula I(a), I(b) or I(c).

3. A compound as claimed in claim 1 wherein each Z independently represents hydrogen, acetyl or benzoyl.

4. A compound as claimed in claim 1 wherein $R^1$ is hydrogen or —CH(OH)CH₂OH.

5. A compound as claimed in claim 1 wherein $R^2$ is methyl, hydrogen, or a sodium, lithium or potassium cation.

6. A compound as claimed in claim 1 wherein $R^3$ is methyl.

7. A compound as claimed in claim 1 wherein n is 1 or 3.

8. A compound as claimed in claim 1, selected from the group consisting of:

O-methyl-4R-[5'-oxy-{N-acetyl-α2"-O-neuramidinyl methyl ester}-2'-oxo-pent-1'-yl]-L-fucopyranoside;

O-methyl-4R-[{N-acetyl-α2"-O-neuramidinyl sodium carboxylate}5'oxy-2'-oxo-pent-1'-yl]-L-fucopyranoside;

O-methyl-4R-[{N-acetyl-α2"-O-neuramidinyl sodium carboxylate}5'oxy-2',3',4'-trihydroxy-pent-1'-yl]-L-fucopyranoside;

O-methyl-4R-[7'-oxy-{N-acetyl-α2"-O-neuramidinyl methyl ester}-2'-hydroxy-hept-3'-en-1'-yl]-L-fucopyranoside; and O-methyl-4R-[7'-oxy-{N-acetyl-α2"-O-neuramidinyl sodium carboxylate}-2'-hydroxy-hept-3'-en-1'-yl]-L-fucopyranoside;

α-O-methyl-2,3-di-O-benzoyl-4R-[5'-oxy-{tetra-O-acetyl-N-acetyl-α2"-O-neuramidinyl methyl ester}-2'-oxo-pent-3'-en-1'-yl]-L-fucopyranoside;

α-O-methyl-2,3-di-O-benzoyl-4R-[{tetra-O-acetyl-N-acetyl-α2"-O-neuramidinyl methyl ester}5'oxy-2'-oxo-pent-1'-yl]-L-fucopyranoside;

α-O-methyl-4R-[5'-oxy-{N-acetyl-α2"-O-neuramidinyl methyl ester}-2'-oxo-pent-1'-yl]-L-fucopyranoside;

α-O-methyl-4R-[{N-acetyl-α2"-O-neuramidinyl sodium carboxylate}5'oxy-2'-oxo-pent-1'-yl]-L-fucopyranoside;

α-O-methyl-2,3-di-O-benzoyl-4R-[{tetra-O-acetyl-N-acetyl-α2"-O-neuramidinyl methyl ester}5'-oxy-2'(R and S)-hydroxy-pent-3'-en-1'-yl]-L-fucopyranoside;

α-O-methyl-4R-[{N-acetyl-α2"-O-neuramidinyl methyl ester}5'-oxy-2'(R and S)-hydroxy-pent-3'-en-1'-yl]-L-fucopyranoside;

α-O-methyl-4R-[{N-acetyl-α2"-O-neuramidinyl sodium carboxylate}5'-oxy-2'(R and S)-hydroxy-pent-3'-en-1'-yl]-L-fucopyranoside;

α-O-methyl-2,3-di-O-benzoyl-4R-[{tetra-O-acetyl-N-acetyl-α2"-O-neuramidinyl methyl ester}5'oxy-2'(R and S)-hydroxy-pent-1'-yl]-L-fucopyranoside;

α-O-methyl-4R-[{N-acetyl-α2"-O-neuramidinyl methyl ester}5'-oxy-2'(R and S)-hydroxy-pent-1'-yl]-L-fucopyranoside;

α-O-methyl-2,3-di-O-benzoyl-4R-[{tetra-O-acetyl-N-acetyl-α2"-O-neuramidinyl methyl ester}5'oxy-2'R,3'R,4'S-trihydroxy-pent-1'-yl]-L-fucopyranoside;

α-O-methyl-2,3-di-O-benzoyl-4R-[{tetra-O-acetyl-N-acetyl-α2"-O-neuramidinyl methyl ester}5'oxy-2'S,3'R,4'S-trihydroxy-pent-1'-yl]-L-fucopyranoside;

α-O-methyl-2,3-di-O-benzoyl-4R-[{tetra-O-acetyl-N-acetyl-α2"-O-neuramidinyl methyl ester}5'oxy-2'R,3'S,4'R-trihydroxy-pent-1'-yl]-L-fucopyranoside;

α-O-methyl-2,3-di-O-benzoyl-4R-[{tetra-O-acetyl-N-acetyl-α2"-O-neuramidinyl methyl ester}5'oxy-2'S,3'S,4'R-trihydroxy-pent-1'-yl]-L-fucopyranoside;

α-O-methyl-4R-[{N-acetyl-α2"-O-neuramidinyl sodium carboxylate}5'oxy-2'R,3'R,4'S-trihydroxy-pent-1'-yl]-L-fucopyranoside;

α-O-methyl-4R-[{N-acetyl-α2"-O-neuramidinyl sodium carboxylate}5'oxy-2'S,3'R,4'S-trihydroxy-pent-1'-yl]-L-fucopyranoside;

α-O-methyl-4R-[{N-acetyl-α2"-O-neuramidinyl sodium carboxylate}5'oxy-2'R,3'S,4'R-trihydroxy-pent-1'-yl]-L-fucopyranoside;

α-O-methyl-4R-[{N-acetyl-α2"-O-neuramidinyl sodium carboxylate}5'oxy-2'S,3'S,4'R-trihydroxy-pent-1'-yl]-L-fucopyranoside;

α-O-methyl-2,3-di-O-benzoyl-4R-[7'-oxy-{tetra-O-acetyl-N-acetyl-α2"-O-neuramidinyl methyl ester}-2'-oxo-hept-3'-en-1'-yl]-L-fucopyranoside;

α-O-methyl-2,3-di-O-benzoyl-4R-[7'-oxy-{tetra-O-acetyl-N-acetyl-α2"-O-neuramidinyl methyl ester}-2'(R and S)-hydroxy-hept-3'-en-1'-yl]-L-fucopyranoside;

α-O-methyl-4R-[7'-oxy-{N-acetyl-α2"-O-neuramidinyl methyl ester}-2'(R and S)-hydroxy-hept-3'-en-1'-yl]-L-fucopyranoside;

α-O-methyl-4R-[7'-oxy-{N-acetyl-α2"-O-neuramidinyl sodium carboxylate}-2'(R and S)-hydroxy-hept-3'-en-1'-yl]-L-fucopyranoside;

α-O-methyl-2,3-di-O-benzoyl-4S-[5'-oxy-{tetra-O-acetyl-N-acetyl-α2"-O-neuramidinyl methyl ester}-2'-oxo-pent-3'-en-1'-yl]-L-fucopyranoside;

α-O-methyl-2,3-di-O-benzoyl-4S-[{tetra-O-acetyl-N-acetyl-α2"-O-neuramidinyl methyl ester}5'-oxy-2'(R and S)-hydroxy-pent-3'-en-1'-yl]-L-fucopyranoside;

α-O-methyl-2-O-benzoyl-4S-[{tetra-O-acetyl-N-acetyl-α2"-O-neuramidinyl methyl ester}5'-oxy-2'(R and S)-hydroxy-pent-3'-en-1'-yl]-L-fucopyranoside; and α-O-methyl-4S-[{N-acetyl-α2"-O-neuramidinyl carboxylic acid}5'-oxy-2'(R and S)-hydroxy-pent-3'-en-1'-yl]-L-fucopyranoside.

9. A process for the preparation of compounds of claim 1 formula (I) wherein X is a divalent group of formula (Ia) and Y is a divalent group of formula (Ih), which process comprises (a) reacting a compound of formula (II):

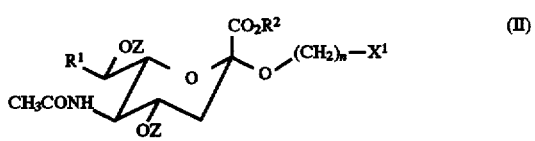

wherein n, $R^1$, $R^2$, and Z are as defined in formula (I), and $X^1$ is an aldehyde group —CHO or a group —$CH_2L$ wherein L is a leaving group, with a compound of formula (III):

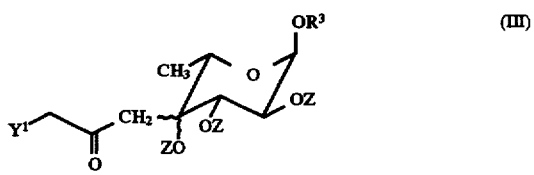

wherein $R^3$ and Z are as defined in formula (I) and $Y^1$ represents an activating group for the methylene group to which it is attached, to form an intermediate of formula (IV)

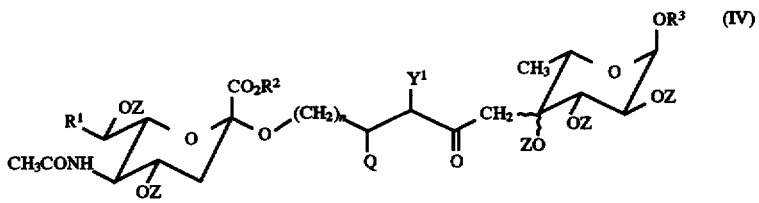

wherein n, $R^1$, $R^2$, $R^3$, Z and $Y^1$ are as defined in formulae (II) and (III) and Q is either (1) OH when $X^1$ in formula (II) is —CHO, or (2) H when $X^1$ in formula (II) is a group —$CH_2L$ wherein L is a leaving group;
and then (b) forming a double bond between the carbon atoms carrying the groups Q and $Y^1$ by either (1) in cases where $X^1$ in compound (II) is an aldehyde group —CHO allowing the said intermediate product to eliminate Q sponaneously and $Y^1$, or treating the said intermediate product to eliminate Q and $Y^1$, or (2) cases where $X^1$ in compound (II) is a group —$CH_2L$ wherein L is a leaving group treating the said intermediate product to eliminate Q and $Y^1$;

and optionally (c) in the resultant compound of formula (I), removing one or more hydroxyl protecting groups Z, and/or hydrolyzing any ester group —$CO_2R^2$ to a carboxylic acid or pharmaceutically acceptable cationic carboxylate group.

10. A process as claimed in claim 9 wherein the activating group $Y^1$ is an alkyl or fluoroalkyl phosphonate, diphenyl phosphine oxide, triphenyl phosphine, phenyl sulfoxide, phenyl sulfonate, or alkyl carboxylate group.

11. A process as claimed in claim 9 wherein $X^1$ in compound (II) is a group —$CH_2L$, and the leaving group L is iodo, bromo, or chloro, or a tosylate or mesylate group.

12. A process as claimed in claim 9 wherein the activating group $Y^1$ is an alkyl or fluoroalkyl phosphonate, diphenyl phosphine oxide, phenyl sulfoxide, phenyl sulfonate, or alkyl carboxylate group, and the reaction of compounds (II) and (III) is carried out in the presence of a base to form an enolate of compound (III).

13. A process as claimed in claim 9 wherein the activating group $Y^1$ is an alkyl or fluoroalkyl phosphonate, and $X^1$ in compound (II) is a group —CHO, and the reaction is carried out in the presence of cesium carbonate in t-butanol at a temperature in the range 25°–35° C.

14. A process for the preparation of compounds of claim 1 formula (I) wherein X is a divalent group of formula (Ia) and Y is a bond which process comprises coupling a sialic acid derivative of formula (V);

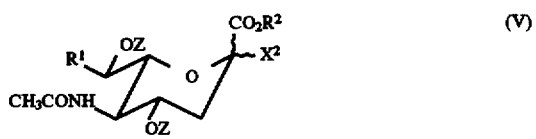

wherein $R^1$, $R^2$ and Z are as defined in formula (I) and $X^2$ is a leaving group, with an alcohol of formula (VI):

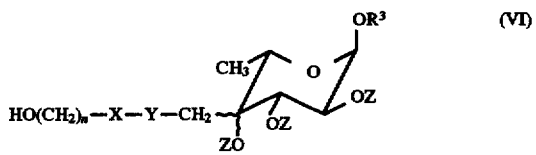

wherein n, $R^3$ and Z are as defined in formula (I), X is a divalent group of formula (Ia) above and Y is bond, and if desired removing one or more hydroxyl protecting groups Z, and/or hydrolyzing any ester group —$CO_2R^2$ to a carboxylic acid or pharmaceutically acceptable cationic carboxylate group.

15. A process as claimed in claim 14 wherein the leaving group $X^2$ in the sialic acid derivative of formula (V) is iodo, bromo, and chloro; a sulfonyl ester such as tosylate, mesylate, triflate or other sulfonyl ester; methylthio, substituted phenylthio or other sulfide group; trichloroacetimidate; or an alpha-S—(=S)—OEt or alpha-O—P(OEt)$_2$ group.

16. A process as claimed in claim 9 or claim 14 which comprises an additional step selected from the group consisting of the following steps (a)–(g):

(a) hydrogenation of a C=C double bond of a compound of formula (I) wherein X=(Ia) to form a compound of formula (I) wherein X=(Ib);

(b) dihydroxylation of a compound of formula (I) wherein X=(Ia) to form a compound of formula (I) wherein X=(Ic);

(c) epoxidation of a compound of formula (I) wherein X=(Ia) to form a compound of formula (I) wherein X=(Id);

(d) cyclopropanation of a compound of formula (I) wherein X=(Ia) to form a compound of formula (I) wherein X=(Ie);

(e) Diels-Alder reaction between a compound of formula (I), X=(Ia) and a diene to form a compound of formula (I) wherein X=(If) or (Ig);

(f) reduction of the ketone group (Ih) of a compound of formula (I), wherein X=(Ia) and Y=(Ih) followed by one of the preceding steps to form a compound of formula (I) wherein X=(Ia)–(Ig) and Y=(Ii); or (g) reaction of a glycosyl donor, a promoter and a compound of formula (I) wherein Y=(Ii) to form a compound of formula (I) wherein X=(Ia) to (Ig) and Y=(Ij)).

17. A method of treatment of (a) a condition mediated by excess accumulation of neutrophils in tissue in a mammal, and/or (b) metastasis in which neutrophils or tumor cells leave the circulation and infiltrate tissue in a mammal, which method comprises administering to said mammal an effect amount of a compound as claimed in claim 1, or a pharmaceutically acceptable salt, hydrate, or solvate thereof.

18. The method of claim 17, wherein either an inflammatory condition or tumor metastasis is treated.

19. The method of claim 17, wherein the condition is Adult Respiratory Distress Syndrome (ARDS), asthma, reperfusion injury following myocardial infarction, stroke, transplant rejection, inflammatory bowel disease, rheumatoid arthritis, or endotoxic hemorrhagic shock.

20. The method of claim 17, wherein the condition is chronic skin inflammation, psoriasis, lichen planus, or nonspecific contact dermatitis in which higher than normal levels of skin-homing memory T cells are implicated.

21. A pharmaceutical or veterinary composition comprising a compound as claimed in claim 1, or a pharmaceutically acceptable salt, hydrate, or solvate thereof, together with a pharmaceutically or veterinarily acceptable excipient or carrier.

* * * * *